US007723560B2

(12) United States Patent
Lockwood et al.

(10) Patent No.: US 7,723,560 B2
(45) Date of Patent: May 25, 2010

(54) WOUND VACUUM THERAPY DRESSING KIT

(76) Inventors: Jeffrey S. Lockwood, 500 N. Walnut, Indianapolis, IN (US) 47006; Robert Petrosenko, 189 Corn Planters St., Charleston, SC (US) 29492

( * ) Notice: Subject to any disclaimer, the term of this patent is extended or adjusted under 35 U.S.C. 154(b) by 114 days.

(21) Appl. No.: 10/496,360

(22) PCT Filed: Dec. 20, 2002

(86) PCT No.: PCT/US02/41231

§ 371 (c)(1),
(2), (4) Date: May 21, 2004

(87) PCT Pub. No.: WO03/057307

PCT Pub. Date: Jul. 17, 2003

(65) Prior Publication Data

US 2004/0243073 A1 Dec. 2, 2004

Related U.S. Application Data

(60) Provisional application No. 60/344,620, filed on Dec. 26, 2001.

(51) Int. Cl.
*A61F 13/00* (2006.01)
*A61F 13/02* (2006.01)
*A61F 15/00* (2006.01)

(52) U.S. Cl. .............................. 602/45; 602/41; 602/54; 602/59; 604/304; 604/305; 604/307

(58) Field of Classification Search ................. 604/301, 604/304, 305, 307; 602/42, 45, 59
See application file for complete search history.

(56) References Cited

U.S. PATENT DOCUMENTS 774,529 A 11/1904 Nieschang (Continued)

FOREIGN PATENT DOCUMENTS

AU 550575 A1 8/1982

(Continued)

OTHER PUBLICATIONS

International Search Report for WO 03045492, Lockwood et al., Jun. 2003.

(Continued)

*Primary Examiner*—Melanie J Hand

(57) ABSTRACT

A wound vacuum therapy dressing kit is provided for use with a wound drainage system having a vacuum source. The kit may include a wound dressing member, a sealing film, and a wound measurement device. The wound dressing member may include a wound contacting surface configured to be in contact with and generally conform to a wound surface of a patient. The member may be adapted to be coupled to the vacuum source for communicating suction from the vacuum source to the wound surface. The sealing film of the kit may be provided for placement over the member and may be configured to adhere to a patient's healthy skin surrounding the wound. The wound measurement device may include a transparent top portion and a transparent bottom portion configured for placement adjacent the wound surface. The top portion may include a drawing surface and a grid associated with the drawing surface.

22 Claims, 7 Drawing Sheets

U.S. PATENT DOCUMENTS

| | | |
|---|---|---|
| 1,000,001 A | 8/1911 | Holz |
| 1,355,846 A | 10/1920 | Rannells |
| 1,385,346 A | 7/1921 | Taylor |
| 1,709,520 A | 4/1929 | Chandler |
| 1,936,129 A | 11/1933 | Fisk |
| 2,078,180 A | 4/1937 | Kronenberg |
| 2,195,771 A | 4/1940 | Estler |
| 2,221,758 A | 11/1940 | Elmquist |
| 2,338,339 A | 1/1944 | LaMere et al. |
| 2,443,481 A | 6/1948 | Sene |
| 2,547,758 A | 4/1951 | Keeling ................ 128/349 |
| 2,560,915 A | 7/1951 | Bamberger ............. 128/350 |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans et al. |
| 2,910,763 A | 11/1959 | Lauterbach ............. 128/72.2 |
| 2,969,057 A | 1/1961 | Simmons ................... 128/2 |
| 3,026,874 A | 3/1962 | Stevens |
| 3,066,672 A | 12/1962 | Crosby, Jr. et al. ......... 128/276 |
| 3,315,665 A | 4/1967 | MacLeod |
| 3,367,332 A | 2/1968 | Groves |
| 3,382,867 A | 5/1968 | Reaves |
| 3,430,631 A | 3/1969 | Abramson ............... 128/350 |
| 3,492,991 A | 2/1970 | Dyer, Jr. |
| 3,520,300 A | 7/1970 | Flower, Jr. |
| 3,528,416 A | 9/1970 | Chamberlain |
| 3,568,675 A | 3/1971 | Harvey |
| 3,585,742 A | 6/1971 | Tyler |
| 3,599,639 A | 8/1971 | Spotz |
| 3,610,238 A | 10/1971 | Rich, Jr. |
| 3,623,087 A | 11/1971 | Gallichotte |
| 3,626,087 A | 12/1971 | Tomioka ................. 178/5.4 |
| 3,648,692 A | 3/1972 | Wheeler |
| 3,682,180 A | 8/1972 | McFarlane ............... 128/350 |
| 3,683,894 A | 8/1972 | Villari |
| 3,721,244 A | 3/1973 | Elmaleh |
| 3,752,158 A | 8/1973 | Kariher |
| 3,753,439 A | 8/1973 | Brugarolas et al. ......... 128/350 |
| 3,782,377 A | 1/1974 | Rychlik |
| 3,812,972 A | 5/1974 | Rosenblum |
| 3,814,095 A | 6/1974 | Lubens |
| 3,817,145 A | 6/1974 | Cohen ..................... 84/471 |
| 3,823,720 A | 7/1974 | Tribble ................... 128/350 |
| 3,826,254 A | 7/1974 | Mellor ................... 128/133 |
| 3,831,588 A | 8/1974 | Rinder |
| 3,860,008 A | 1/1975 | Miner et al. .............. 128/350 |
| 3,874,387 A | 4/1975 | Barbieri |
| 3,903,882 A | 9/1975 | Augurt |
| 3,924,624 A | 12/1975 | Schachet ................. 128/276 |
| 3,935,863 A | 2/1976 | Kliger |
| 3,954,105 A | 5/1976 | Nordby et al. |
| 3,982,546 A | 9/1976 | Friend |
| 4,004,590 A | 1/1977 | Muriot |
| 4,013,076 A | 3/1977 | Puderbaugh et al. |
| RE29,319 E | 7/1977 | Nordby et al. |
| RE029,321 E | 7/1977 | Holbrook |
| 4,058,123 A | 11/1977 | May ..................... 128/278 |
| 4,080,970 A | 3/1978 | Miller |
| 4,096,853 A | 6/1978 | Weigand ................... 128/2 |
| 4,112,947 A | 9/1978 | Nehring |
| 4,139,004 A | 2/1979 | Gonzalez, Jr. |
| 4,149,541 A | 4/1979 | Gammons et al. |
| 4,165,748 A | 8/1979 | Johnson ................. 128/348 |
| 4,178,974 A | 12/1979 | Levin |
| 4,184,510 A | 1/1980 | Murry et al. .............. 137/565 |
| 4,191,204 A | 3/1980 | Nehring |
| 4,224,941 A | 9/1980 | Stivala |
| 4,233,969 A | 11/1980 | Lock et al. ............... 128/156 |
| 4,245,630 A | 1/1981 | Lloyd et al. .............. 128/155 |
| 4,250,882 A | 2/1981 | Adair |
| 4,256,109 A | 3/1981 | Nichols .................. 128/276 |
| 4,261,363 A | 4/1981 | Russo .................... 128/350 |
| 4,275,721 A | 6/1981 | Olson |
| 4,284,079 A | 8/1981 | Adair .................... 128/295 |
| 4,297,995 A | 11/1981 | Golub |
| 4,333,468 A | 6/1982 | Geist .................... 128/348 |
| 4,341,209 A | 7/1982 | Schaar |
| 4,373,519 A | 2/1983 | Errede et al. ............. 128/156 |
| 4,382,441 A | 5/1983 | Svedman |
| 4,392,853 A | 7/1983 | Muto ..................... 604/171 |
| 4,392,858 A | 7/1983 | George et al. ............. 604/187 |
| 4,399,816 A | 8/1983 | Spangler |
| 4,419,097 A | 12/1983 | Rowland .................. 604/174 |
| 4,457,755 A | 7/1984 | Wilson |
| 4,460,370 A | 7/1984 | Allison et al. |
| 4,465,062 A | 8/1984 | Versaggi et al. |
| 4,465,485 A | 8/1984 | Kashmer et al. ........... 604/320 |
| 4,469,092 A | 9/1984 | Marshall et al. |
| 4,475,909 A | 10/1984 | Eisenberg ................ 604/349 |
| 4,480,638 A | 11/1984 | Schmid .................. 128/155 |
| 4,508,533 A | 4/1985 | Abramson ................. 604/35 |
| 4,525,156 A | 6/1985 | Benusa et al. ............. 604/28 |
| 4,525,166 A | 6/1985 | Leclerc |
| 4,525,374 A | 6/1985 | Vaillancourt ............... 427/2 |
| 4,533,352 A | 8/1985 | Van Beek et al. |
| 4,533,419 A * | 8/1985 | Pieslak et al. ............. 156/85 |
| 4,540,412 A | 9/1985 | Van Overloop |
| 4,543,100 A | 9/1985 | Brodsky .................. 604/180 |
| 4,548,202 A | 10/1985 | Duncan .................. 128/334 |
| 4,551,139 A | 11/1985 | Plaas et al. .............. 604/290 |
| 4,553,967 A | 11/1985 | Ferguson et al. |
| 4,569,348 A | 2/1986 | Hasslinger ............... 604/179 |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,614,794 A | 9/1986 | Easton et al. ............. 530/356 |
| 4,624,656 A | 11/1986 | Clark et al. |
| 4,633,863 A | 1/1987 | Filips et al. |
| 4,637,819 A | 1/1987 | Ouellette et al. |
| 4,640,688 A | 2/1987 | Hauser ................... 604/352 |
| 4,641,643 A | 2/1987 | Greer |
| 4,645,492 A | 2/1987 | Weeks |
| 4,655,210 A | 4/1987 | Edenbaum et al. |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. ............. 604/67 |
| 4,713,051 A | 12/1987 | Steppe et al. .............. 604/30 |
| 4,717,332 A | 1/1988 | Edens ..................... 431/8 |
| 4,717,382 A | 1/1988 | Clemens et al. |
| 4,733,659 A | 3/1988 | Edenbaum et al. |
| 4,735,606 A | 4/1988 | Davison |
| 4,735,610 A | 4/1988 | Akkas et al. |
| 4,740,202 A | 4/1988 | Stacey et al. |
| 4,743,232 A | 5/1988 | Kruger |
| 4,747,166 A | 5/1988 | Kuntz |
| 4,758,220 A | 7/1988 | Sundblom et al. ........... 604/65 |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,787,888 A | 11/1988 | Fox ....................... 604/20 |
| 4,798,578 A | 1/1989 | Ranford |
| 4,820,265 A | 4/1989 | DeSatnick et al. |
| 4,820,284 A | 4/1989 | Hauri |
| 4,826,494 A | 5/1989 | Richmond et al. .......... 604/323 |
| 4,826,949 A | 5/1989 | Stanko ................... 528/272 |
| 4,834,110 A | 5/1989 | Richard |

| | | | |
|---|---|---|---|
| 4,838,883 A | 6/1989 | Matsuura .................... 604/349 |
| 4,840,187 A | 6/1989 | Brazier ...................... 128/844 |
| 4,841,962 A | 6/1989 | Berg et al. .................. 128/156 |
| 4,850,350 A | 7/1989 | Jackson ................ 128/207.16 |
| 4,863,449 A | 9/1989 | Therriault et al. ........... 604/352 |
| 4,872,450 A | 10/1989 | Austad |
| 4,878,901 A | 11/1989 | Sachse ....................... 604/174 |
| 4,890,608 A | 1/1990 | Steer |
| 4,897,081 A | 1/1990 | Poirier et al. |
| 4,900,302 A | 2/1990 | Newton ........................ 604/30 |
| 4,902,508 A | 2/1990 | Badylak et al. ............... 424/95 |
| 4,906,233 A | 3/1990 | Moriuchi et al. ............ 604/174 |
| 4,906,240 A | 3/1990 | Reed et al. |
| 4,915,694 A | 4/1990 | Yamamoto et al. |
| 4,917,112 A | 4/1990 | Kalt |
| 4,919,654 A | 4/1990 | Kalt ........................... 604/180 |
| 4,921,492 A | 5/1990 | Schultz et al. |
| 4,930,997 A | 6/1990 | Bennett |
| 4,941,882 A | 7/1990 | Ward et al. |
| 4,953,565 A | 9/1990 | Tachibana et al. |
| 4,956,178 A | 9/1990 | Badylak et al. ............. 424/551 |
| 4,957,492 A | 9/1990 | McVay |
| 4,962,761 A | 10/1990 | Golden |
| 4,969,880 A | 11/1990 | Zamierowski |
| 4,969,881 A | 11/1990 | Viesturs |
| 4,970,298 A | 11/1990 | Silver et al. ................. 530/356 |
| 4,985,019 A | 1/1991 | Michelson .................. 604/180 |
| 4,988,336 A | 1/1991 | Kohn |
| 4,990,144 A | 2/1991 | Blott |
| 4,991,574 A | 2/1991 | Pocknell |
| 4,994,022 A | 2/1991 | Steffler et al. |
| 4,997,425 A | 3/1991 | Shioya et al. |
| 5,000,172 A * | 3/1991 | Ward ........................... 602/52 |
| 5,000,741 A | 3/1991 | Kalt |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,035,865 A | 7/1991 | Inaba et al. |
| 5,037,397 A | 8/1991 | Kalt et al. .................... 604/174 |
| 5,042,978 A | 8/1991 | Quenin et al. |
| 5,045,777 A | 9/1991 | Itagaki |
| 5,060,662 A | 10/1991 | Farnsworth, III |
| 5,071,409 A | 12/1991 | Rosenberg |
| 5,073,172 A | 12/1991 | Fell |
| 5,080,650 A | 1/1992 | Hirsch et al. ................. 604/104 |
| 5,086,170 A | 2/1992 | Luheshi et al. ............... 540/303 |
| 5,086,763 A | 2/1992 | Hathman |
| 5,086,764 A | 2/1992 | Gilman |
| 5,092,858 A | 3/1992 | Benson et al. ............... 604/319 |
| 5,100,396 A | 3/1992 | Zamierowski |
| 5,101,808 A | 4/1992 | Kobayashi et al. |
| 5,106,362 A | 4/1992 | Gilman |
| 5,106,629 A | 4/1992 | Cartmell et al. |
| 5,134,994 A | 8/1992 | Say ........................ 128/200.24 |
| 5,135,518 A | 8/1992 | Vera |
| 5,146,925 A | 9/1992 | Snow |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,167,622 A | 12/1992 | Muto ........................... 604/35 |
| 5,170,781 A | 12/1992 | Loomis |
| 5,176,502 A | 1/1993 | Sanderson et al. |
| 5,176,663 A | 1/1993 | Svedman et al. |
| 5,176,667 A | 1/1993 | DeBring |
| 5,181,908 A | 1/1993 | Bell ............................. 604/24 |
| 5,189,609 A | 2/1993 | Tivig et al. |
| 5,197,948 A | 3/1993 | Ghodsian .................... 604/30 |
| 5,215,522 A | 6/1993 | Page et al. .................... 604/33 |
| 5,215,539 A | 6/1993 | Schoolman |
| 5,224,929 A | 7/1993 | Remiszewski ............... 604/30 |
| 5,228,431 A | 7/1993 | Giarretto |
| 5,230,350 A | 7/1993 | Fentress |
| 5,232,453 A | 8/1993 | Plass et al. .................. 604/180 |
| 5,238,654 A | 8/1993 | Nohl et al. |
| 5,249,121 A | 9/1993 | Baum et al. |
| 5,256,418 A | 10/1993 | Kemp et al. ................. 424/423 |
| 5,261,893 A | 11/1993 | Zamierowski |
| 5,263,922 A | 11/1993 | Sova et al. |
| 5,265,605 A * | 11/1993 | Afflerbach .................. 600/300 |
| 5,275,826 A | 1/1994 | Badylak et al. .............. 424/551 |
| 5,278,100 A | 1/1994 | Doan et al. .................. 437/200 |
| 5,279,550 A | 1/1994 | Habib et al. ................... 604/38 |
| 5,281,422 A | 1/1994 | Badylak et al. .............. 424/551 |
| 5,291,887 A | 3/1994 | Stanley et al. |
| 5,298,015 A | 3/1994 | Komatsuzaki et al. |
| 5,314,409 A | 5/1994 | Sarosiek et al. ............. 604/101 |
| 5,330,452 A | 7/1994 | Zook |
| 5,335,651 A | 8/1994 | Foster et al. |
| 5,338,293 A | 8/1994 | Jeppsson et al. .............. 604/29 |
| 5,342,293 A | 8/1994 | Zanger |
| 5,342,301 A | 8/1994 | Saab .......................... 604/96 |
| 5,342,376 A | 8/1994 | Ruff .......................... 606/151 |
| 5,344,415 A | 9/1994 | DeBusk et al. |
| 5,349,965 A | 9/1994 | McCarver |
| 5,352,463 A | 10/1994 | Badylak et al. .............. 424/551 |
| 5,358,494 A | 10/1994 | Svedman |
| 5,370,610 A | 12/1994 | Reynolds ...................... 604/43 |
| 5,372,821 A | 12/1994 | Badylak et al. .............. 424/551 |
| 5,374,254 A | 12/1994 | Buma |
| 5,376,252 A | 12/1994 | Ekstrom et al. |
| 5,380,280 A | 1/1995 | Peterson |
| 5,395,315 A | 3/1995 | Griep |
| 5,409,013 A | 4/1995 | Clement ...................... 128/753 |
| 5,413,788 A | 5/1995 | Edwards et al. |
| 5,419,768 A | 5/1995 | Kayser |
| 5,431,622 A | 7/1995 | Pyrozyk et al. |
| 5,437,622 A | 8/1995 | Carion ........................ 602/57 |
| 5,437,651 A | 8/1995 | Todd et al. |
| 5,445,604 A | 8/1995 | Lang |
| 5,445,833 A | 8/1995 | Badylak et al. .............. 424/551 |
| 5,447,505 A | 9/1995 | Valentine et al. |
| 5,449,383 A | 9/1995 | Chatelier et al. ................ 623/1 |
| 5,451,215 A | 9/1995 | Wolter |
| 5,451,373 A | 9/1995 | Lewis et al. |
| 5,478,333 A | 12/1995 | Asherman, Jr. |
| 5,484,420 A | 1/1996 | Russo |
| 5,484,427 A | 1/1996 | Gibbons |
| 5,484,428 A | 1/1996 | Drainville et al. |
| 5,487,889 A | 1/1996 | Eckert et al. |
| 5,516,533 A | 5/1996 | Badylak et al. .............. 424/551 |
| 5,520,652 A | 5/1996 | Peterson |
| 5,527,293 A | 6/1996 | Zamierowski |
| 5,531,670 A | 7/1996 | Westby et al. |
| 5,533,981 A | 7/1996 | Mandro et al. |
| 5,534,346 A * | 7/1996 | Robinson .................... 428/343 |
| 5,542,918 A | 8/1996 | Atkinson |
| 5,549,584 A | 8/1996 | Gross |
| 5,554,389 A | 9/1996 | Badylak et al. .............. 424/558 |
| 5,556,375 A | 9/1996 | Ewall |
| 5,558,639 A | 9/1996 | Gangemi et al. |
| 5,573,784 A | 11/1996 | Badylak et al. .............. 424/551 |
| 5,578,022 A | 11/1996 | Scherson et al. |
| 5,578,662 A | 11/1996 | Bennett et al. ................ 524/54 |
| 5,607,388 A | 3/1997 | Ewall |
| 5,621,035 A | 4/1997 | Lyles et al. .................. 524/404 |
| 5,624,418 A | 4/1997 | Shepard |
| 5,628,735 A | 5/1997 | Skow |
| 5,629,186 A | 5/1997 | Yasukawa et al. ........... 435/177 |
| 5,631,011 A | 5/1997 | Wadström ................... 424/400 |
| 5,635,201 A | 6/1997 | Fabo |
| 5,636,643 A | 6/1997 | Argenta et al. |

| Patent No. | Date | Name | Ref |
|---|---|---|---|
| 5,641,518 A | 6/1997 | Badylak et al. | 424/551 |
| 5,645,081 A | 7/1997 | Argenta et al. | |
| 5,645,860 A | 7/1997 | Knapp et al. | 424/551 |
| 5,655,258 A | 8/1997 | Heintz | |
| 5,656,027 A | 8/1997 | Ellingboe | |
| 5,662,598 A | 9/1997 | Tobin | |
| 5,662,624 A | 9/1997 | Sundstrom et al. | |
| 5,662,625 A | 9/1997 | Westwood | |
| 5,669,892 A | 9/1997 | Keogh et al. | |
| 5,672,152 A | 9/1997 | Mason et al. | |
| 5,674,193 A | 10/1997 | Hayes | 604/28 |
| 5,678,564 A | 10/1997 | Lawrence et al. | |
| 5,681,290 A | 10/1997 | Alexander | |
| 5,690,815 A | 11/1997 | Krasnoff et al. | |
| 5,695,998 A | 12/1997 | Badylak et al. | 435/391 |
| 5,697,920 A | 12/1997 | Gibbons | |
| 5,711,969 A | 1/1998 | Patel et al. | 424/551 |
| 5,718,955 A | 2/1998 | McGuire et al. | |
| 5,735,833 A | 4/1998 | Olson | |
| 5,741,237 A | 4/1998 | Walker | |
| 5,749,842 A * | 5/1998 | Cheong et al. | 602/41 |
| 5,753,267 A | 5/1998 | Badylak et al. | 424/551 |
| 5,755,791 A | 5/1998 | Whitson et al. | 623/15 |
| 5,759,570 A | 6/1998 | Arnold | |
| 5,762,640 A | 6/1998 | Kajiwara et al. | |
| 5,762,966 A | 6/1998 | Knapp et al. | 424/551 |
| 5,780,281 A | 7/1998 | Yasukawa et al. | 435/176 |
| 5,782,871 A | 7/1998 | Fujiwara et al. | |
| 5,795,584 A | 8/1998 | Totakura et al. | 424/426 |
| 5,800,383 A | 9/1998 | Chandler et al. | 604/35 |
| 5,817,145 A | 10/1998 | Augustine et al. | |
| 5,827,246 A | 10/1998 | Bowen | |
| 5,827,296 A | 10/1998 | Morris et al. | |
| 5,855,619 A | 1/1999 | Caplan et al. | 623/11 |
| 5,866,414 A | 2/1999 | Badylak et al. | 435/325 |
| 5,881,723 A | 3/1999 | Wallace et al. | |
| 5,902,874 A | 5/1999 | Roby et al. | 528/310 |
| 5,902,875 A | 5/1999 | Roby et al. | 528/310 |
| 5,911,222 A | 6/1999 | Lawrence et al. | |
| 5,914,387 A | 6/1999 | Roby et al. | 528/310 |
| 5,919,476 A | 7/1999 | Fischer et al. | |
| 5,921,972 A | 7/1999 | Skow | |
| 5,928,174 A | 7/1999 | Gibbins | |
| 5,931,304 A | 8/1999 | Hammond | |
| 5,941,859 A | 8/1999 | Lerman | |
| 5,942,496 A | 8/1999 | Bonadio et al. | 514/44 |
| 5,947,914 A | 9/1999 | Augustine | |
| 5,951,295 A | 9/1999 | Lyles et al. | 433/228.1 |
| 5,954,680 A | 9/1999 | Augustine | |
| 5,961,480 A | 10/1999 | Augustine | |
| 5,962,427 A | 10/1999 | Goldstein et al. | 514/44 |
| 5,964,721 A | 10/1999 | Augustine | |
| 5,964,723 A | 10/1999 | Augustine | |
| 5,986,163 A | 11/1999 | Augustine | |
| 5,997,568 A | 12/1999 | Liu | 606/228 |
| 6,010,527 A | 1/2000 | Augustine et al. | |
| 6,013,048 A | 1/2000 | Podany et al. | 604/22 |
| 6,017,493 A | 1/2000 | Cambron et al. | |
| 6,039,724 A | 3/2000 | Seifert et al. | |
| 6,045,518 A | 4/2000 | Augustine | |
| 6,045,541 A | 4/2000 | Matsumoto et al. | |
| 6,051,747 A | 4/2000 | Lindqvist et al. | |
| 6,056,730 A | 5/2000 | Greter | |
| 6,071,254 A | 6/2000 | Augustine | |
| 6,071,267 A | 6/2000 | Zamierowski | |
| 6,071,304 A | 6/2000 | Augustine et al. | |
| 6,080,189 A | 6/2000 | Augustine et al. | |
| 6,080,243 A | 6/2000 | Insley et al. | |
| 6,093,160 A | 7/2000 | Augustine et al. | |
| 6,093,230 A | 7/2000 | Johnson, III et al. | |
| 6,095,992 A | 8/2000 | Augustine | |
| 6,099,567 A | 8/2000 | Badylak et al. | 623/13 |
| 6,110,197 A | 8/2000 | Augustine et al. | |
| 6,113,561 A | 9/2000 | Augustine | |
| 6,117,111 A | 9/2000 | Fleischmann | |
| 6,135,116 A | 10/2000 | Vogel et al. | |
| 6,142,982 A | 11/2000 | Hunt et al. | |
| 6,143,945 A | 11/2000 | Augustine et al. | |
| 6,149,614 A | 11/2000 | Dunshee et al. | |
| 6,171,344 B1 | 1/2001 | Atala | 623/23.64 |
| 6,174,306 B1 | 1/2001 | Fleischmann | |
| 6,203,563 B1 | 3/2001 | Fernandez | |
| 6,206,931 B1 | 3/2001 | Cook et al. | 623/23.75 |
| 6,207,875 B1 | 3/2001 | Lindqvist et al. | |
| 6,213,965 B1 | 4/2001 | Augustine et al. | |
| 6,213,966 B1 | 4/2001 | Augustine | |
| 6,217,535 B1 | 4/2001 | Augustine | |
| 6,235,009 B1 | 5/2001 | Skow | |
| 6,235,047 B1 | 5/2001 | Augustine et al. | 607/96 |
| 6,241,697 B1 | 6/2001 | Augustine | |
| 6,241,698 B1 | 6/2001 | Augustine | |
| 6,241,747 B1 | 6/2001 | Ruff | 606/216 |
| 6,244,311 B1 | 6/2001 | Hand et al. | |
| 6,244,698 B1 | 6/2001 | Hand et al. | |
| 6,248,084 B1 | 6/2001 | Augustine et al. | |
| 6,254,557 B1 | 7/2001 | Augustine et al. | |
| 6,254,580 B1 | 7/2001 | Svedman | |
| 6,259,067 B1 | 7/2001 | Faries, Jr. et al. | |
| 6,264,622 B1 | 7/2001 | Augustine | |
| 6,264,979 B1 | 7/2001 | Svedman | |
| 6,267,740 B1 | 7/2001 | Augustine et al. | |
| 6,283,931 B1 | 9/2001 | Augustine | |
| 6,284,941 B1 | 9/2001 | Cox et al. | |
| 6,287,316 B1 | 9/2001 | Agarwal et al. | 606/151 |
| 6,290,685 B1 | 9/2001 | Insley et al. | |
| 6,293,917 B1 | 9/2001 | Augustine et al. | |
| 6,325,788 B1 | 12/2001 | Edwards et al. | 606/41 |
| 6,345,623 B1 | 2/2002 | Heaton et al. | |
| 6,364,853 B1 | 4/2002 | French et al. | 604/35 |
| 6,394,142 B1 | 5/2002 | Woelfel et al. | 138/115 |
| 6,398,767 B1 | 6/2002 | Fleischmann | |
| 6,410,427 B1 | 6/2002 | Hu | 38/655 |
| 6,440,427 B1 | 8/2002 | Wadström | 424/400 |
| 6,458,109 B1 | 10/2002 | Henley et al. | |
| 6,471,685 B1 | 10/2002 | Johnson | |
| 6,472,581 B1 | 10/2002 | Muramatsu et al. | |
| 6,488,643 B1 | 12/2002 | Tumey et al. | 602/13 |
| 6,491,682 B2 | 12/2002 | Paderni | |
| 6,491,693 B1 | 12/2002 | Lytinas | |
| 6,493,568 B1 | 12/2002 | Bell et al. | 600/323 |
| 6,500,112 B1 | 12/2002 | Khouri | |
| 6,520,982 B1 | 2/2003 | Boynton et al. | |
| 6,553,998 B2 | 4/2003 | Heaton et al. | |
| 6,557,704 B1 | 5/2003 | Randolph | |
| 6,559,773 B1 | 5/2003 | Berry | |
| 6,599,277 B2 | 7/2003 | Neubert | |
| 6,626,891 B2 | 9/2003 | Ohmstede | |
| 6,638,270 B2 | 10/2003 | Johnson | |
| 6,648,862 B2 | 11/2003 | Watson | |
| 6,663,349 B1 | 12/2003 | Discenzo et al. | |
| 6,685,681 B2 | 2/2004 | Lockwood et al. | |
| 6,691,047 B1 | 2/2004 | Fredericks | |
| 6,695,823 B1 | 2/2004 | Lina et al. | |
| 6,695,824 B2 | 2/2004 | Howard et al. | |
| 6,719,779 B2 | 4/2004 | Daoud | |
| 6,749,592 B2 | 6/2004 | Lord | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,936,037 B2 | 8/2005 | Bubb et al. | |

| | | | | | | |
|---|---|---|---|---|---|---|
| 6,951,553 | B2 | 10/2005 | Bubb et al. | 2007/0014837 A1 | 1/2007 | Johnson et al. |
| 6,966,889 | B2 | 11/2005 | Saab ................. 604/96.01 | 2007/0021697 A1 | 1/2007 | Ginther et al. |
| 6,979,324 | B2 | 12/2005 | Bybordi et al. | 2007/0021698 A1 | 1/2007 | Fleischmann |
| 6,994,702 | B1 | 2/2006 | Johnson | 2007/0032778 A1 | 2/2007 | Heaton et al. |
| 6,994,708 | B2 | 2/2006 | Johnson | 2007/0038172 A1 | 2/2007 | Zamierowski |
| 7,004,915 | B2 | 2/2006 | Boynton et al. | 2007/0156104 A1 | 7/2007 | Lockwood et al. |

FOREIGN PATENT DOCUMENTS

| | | |
|---|---|---|
| AU | 745271 | 4/1999 |
| AU | 755496 | 2/2002 |
| CA | 1127488 | 7/1982 |
| CA | 2005436 | 6/1990 |
| CA | 2303085 | 3/1999 |
| DE | 0372727 | 3/1923 |
| DE | 26 40 413 A1 | 3/1978 |
| DE | 28 09 828 A1 | 9/1978 |
| DE | 3102674 A1 | 9/1982 |
| DE | 3539533 A1 | 5/1987 |
| DE | 40 12 232 | 10/1991 |
| DE | 4111122 A1 | 4/1993 |
| DE | 43 06 478 A1 | 9/1994 |
| DE | 29504378 U1 | 10/1995 |
| DE | 29715634 | 11/1997 |
| DE | 19722075 C1 | 10/1998 |
| DK | 0064055 | 10/1945 |
| EP | 0 100 148 A1 | 2/1984 |
| EP | 0117632 A2 | 9/1984 |
| EP | 0 161 865 A2 | 11/1985 |
| EP | 0 358 302 A2 | 3/1990 |
| EP | 0424165 A1 | 4/1991 |
| EP | 0485657 A1 | 5/1992 |
| EP | 0547496 A1 | 6/1993 |
| EP | 0853 950 A1 | 7/1998 |
| EP | 0 777 504 B1 | 10/1998 |
| EP | 0 880 953 A2 | 12/1998 |
| EP | 1 088 569 A2 | 4/2001 |
| EP | 1100574 | 5/2001 |
| EP | 1 190 732 A1 | 3/2002 |
| EP | 1 018 967 B1 | 8/2004 |
| EP | 1726276 | 11/2006 |
| FR | 500253 | 3/1920 |
| FR | 1303238 | 7/1962 |
| GB | 3090 | 6/1902 |
| GB | 641061 | 8/1950 |
| GB | 692578 | 6/1953 |
| GB | 1549756 | 8/1979 |
| GB | 1584772 | 2/1981 |
| GB | 2 195 255 A | 4/1988 |
| GB | 2 197 789 A | 6/1988 |
| GB | 2220357 A | 1/1990 |
| GB | 2 235 877 A | 3/1991 |
| GB | 2307180 | 5/1997 |
| GB | 2307180 A * | 5/1997 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 6/2000 |
| GB | 2351025 A | 12/2000 |
| GB | 2356148 | 5/2001 |
| HU | 199304 B | 1/1989 |
| HU | 20557 | 4/1990 |
| HU | 51150 | 4/1990 |
| HU | P9006526 | 1/1993 |
| HU | P9302966 | 7/1996 |
| HU | 76351 | 8/1997 |
| HU | 215563 | 8/1997 |
| HU | 1666 | 12/1999 |
| JP | 4-129536 | 4/1992 |
| JP | 6-327761 | 11/1994 |
| SE | 0084485 | 10/1935 |
| SG | 71559 | 4/2002 |

| | | | |
|---|---|---|---|
| 7,022,113 | B2 | 4/2006 | Lockwood et al. |
| 7,070,584 | B2 | 7/2006 | Johnson et al. |
| 7,077,832 | B2 | 7/2006 | Fleischmann |
| 7,108,683 | B2 | 9/2006 | Zamierowski |
| 7,117,869 | B2 | 10/2006 | Heaton et al. |
| 7,128,735 | B2 | 10/2006 | Weston |
| 7,144,390 | B1 | 12/2006 | Hannigan et al. |
| 7,195,624 | B2 | 7/2007 | Lockwood et al. |
| 7,245,291 | B2 | 7/2007 | Sharif et al. |
| 7,276,051 | B1 | 10/2007 | Henley et al. |
| 7,338,482 | B2 | 3/2008 | Lockwood et al. .......... 604/543 |
| 2001/0029956 | A1 | 10/2001 | Argenta et al. |
| 2001/0034499 | A1 | 10/2001 | Sessions et al. |
| 2001/0043943 | A1 | 11/2001 | Coffey |
| 2001/0052681 | A1 | 12/2001 | Deavila |
| 2002/0065494 | A1 | 5/2002 | Lockwood et al. |
| 2002/0077661 | A1 | 6/2002 | Saadat ................. 606/221 |
| 2002/0082668 | A1 | 6/2002 | Ingman |
| 2002/0085952 | A1 | 7/2002 | Ellingboe et al. ............. 422/45 |
| 2002/0115951 | A1 | 8/2002 | Norstrem et al. .............. 602/27 |
| 2002/0115952 | A1 | 8/2002 | Johnson et al. |
| 2002/0120185 | A1 | 8/2002 | Johnson ................. 600/345 |
| 2002/0143286 | A1 | 10/2002 | Tumey |
| 2002/0161317 | A1 | 10/2002 | Risk et al. |
| 2002/0193723 | A1 | 12/2002 | Batdorf, Sr. et al. |
| 2003/0032951 | A1 | 2/2003 | Rittman, III et al. |
| 2003/0077311 | A1 | 4/2003 | Vyakarnam et al. .......... 435/41 |
| 2003/0093041 | A1 | 5/2003 | Risk et al. |
| 2003/0143352 | A1 | 7/2003 | Yang et al. ................. 428/36.9 |
| 2003/0208149 | A1 | 11/2003 | Coffey |
| 2003/0219469 | A1 | 11/2003 | Johnson et al. |
| 2003/0225441 | A1 | 12/2003 | Boynton et al. |
| 2004/0030304 | A1 | 2/2004 | Ingman |
| 2004/0039415 | A1 | 2/2004 | Zamierowski |
| 2004/0064111 | A1 | 4/2004 | Lockwood et al. |
| 2004/0167482 | A1 | 8/2004 | Watson |
| 2004/0225208 | A1 | 11/2004 | Johnson |
| 2004/0243073 | A1 | 12/2004 | Lockwood et al. |
| 2004/0249353 | A1 | 12/2004 | Risks, Jr. et al. |
| 2004/0260230 | A1 | 12/2004 | Randolph |
| 2005/0004534 | A1 | 1/2005 | Lockwood et al. |
| 2005/0010153 | A1 | 1/2005 | Lockwood et al. |
| 2005/0033197 | A1 | 2/2005 | Cottler |
| 2005/0065484 | A1 | 3/2005 | Watson, Jr. |
| 2005/0070858 | A1 | 3/2005 | Lockwood et al. |
| 2005/0085795 | A1 | 4/2005 | Lockwood et al. |
| 2005/0090787 | A1 | 4/2005 | Risk, Jr. et al. |
| 2005/0131327 | A1 | 6/2005 | Lockwood et al. |
| 2005/0177190 | A1 | 8/2005 | Zamierowski |
| 2005/0182445 | A1 | 8/2005 | Zamierowski |
| 2005/0182446 | A1 | 8/2005 | DeSantis ................. 606/222 |
| 2005/0234485 | A1 | 10/2005 | Seegert et al. |
| 2005/0234510 | A1 | 10/2005 | Zamierowski |
| 2005/0240220 | A1 | 10/2005 | Zamierowski |
| 2005/0283105 | A1 | 12/2005 | Heaton et al. |
| 2006/0015087 | A1 | 1/2006 | Risk, Jr. et al. |
| 2006/0029650 | A1 | 2/2006 | Coffey |
| 2006/0029675 | A1 | 2/2006 | Ginther |
| 2006/0041247 | A1 | 2/2006 | Petrosenko et al. |
| 2006/0079852 | A1 | 4/2006 | Bubb et al. |
| 2006/0129137 | A1 | 6/2006 | Lockwood et al. |
| 2006/0149170 | A1 | 7/2006 | Boynton et al. |
| 2006/0149171 | A1 | 7/2006 | Vogel et al. |
| 2006/0173253 | A1 | 8/2006 | Ganapathy et al. |
| 2006/0189910 | A1 | 8/2006 | Johnson et al. |
| 2006/0213527 | A1 | 9/2006 | Argenta et al. |
| 2007/0005028 | A1 | 1/2007 | Risk, Jr. et al. |

| | | |
|---|---|---|
| SU | 587941 | 1/1978 |
| SU | 1268175 A1 | 11/1986 |
| WO | WO80/02182 | 10/1980 |
| WO | WO87/04626 | 8/1987 |
| WO | WO 89/04158 | 5/1989 |
| WO | WO90/10424 | 9/1990 |
| WO | WO 90/11795 | 10/1990 |
| WO | WO 91/00718 | 1/1991 |
| WO | WO9108793 | 6/1991 |
| WO | WO 91/16030 | 10/1991 |
| WO | WO9212750 | 8/1992 |
| WO | WO92/19313 | 11/1992 |
| WO | WO 92/20299 | 11/1992 |
| WO | WO93/09715 | 3/1993 |
| WO | WO 93/09727 | 5/1993 |
| WO | WO 94/00090 | 1/1994 |
| WO | WO 94/20041 | 9/1994 |
| WO | 9605873 | 2/1996 |
| WO | WO 96/05873 | 2/1996 |
| WO | WO 96/15745 | 5/1996 |
| WO | WO97/18007 | 5/1997 |
| WO | WO98/02205 | 1/1998 |
| WO | 9838944 | 9/1998 |
| WO | 9901173 | 1/1999 |
| WO | WO 99/13793 | 3/1999 |
| WO | WO99/23990 | 5/1999 |
| WO | 9959816 | 11/1999 |
| WO | WO 00/07653 | 2/2000 |
| WO | WO 00/15277 | 3/2000 |
| WO | 0021586 | 4/2000 |
| WO | WO 00/21586 | 4/2000 |
| WO | WO 00/26100 | 5/2000 |
| WO | WO00/28890 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | 0185248 | 11/2001 |
| WO | 0189431 | 11/2001 |
| WO | WO 01/85248 A1 | 11/2001 |
| WO | WO 01/89431 | 11/2001 |
| WO | WO02/38091 | 5/2002 |
| WO | 02/43634 A1 | 6/2002 |
| WO | 03005943 | 1/2003 |
| WO | 03045492 | 6/2003 |
| WO | WO03/057071 | 7/2003 |
| WO | WO03/057307 | 7/2003 |
| WO | 2003/101508 | 12/2003 |

OTHER PUBLICATIONS

Abdullah, BJJ, JHK Coll Radio 1, Feb. 21, 2001; vol. 4, pp. 272-273, "A New Method for Fixation of Drainage Catheters".
Osterbroek, R.E. et al., "A Micromachined Pressure/Flow-sensor" (Abstract only), www.ingentaconnect.com/ content/els/09244247/ 1999/00000077/0000003/art00188, Sensor and Actuators A: vol. 77, No. 3, Nov. 2, 1999.
PCT Search Report dated May 9, 2003 for PCT/US02/41231 filed Dec. 20, 2002.
Supplementary European search report dated Apr. 6, 2009 EP 02 79 4394.
"Jump-Start Wound Healing with OASIS," *WOUNDS*, Special Supplement, 13(2):1-28, 2001.
"Oasis™ Wound Dressing," *SIS™Technology*, pp. 1-4, Sep. 2001.
"Surgisis™ Soft-Tissue Graft," *SIS™ Technology*, pp. 1-4, Sep. 2001.
Brochure—"Cavi-Care," *Smith & Nephew*, 2000.
Brochure—Healthpoint® Oasis® Wound Matrix, *Cook Biotech Incorporated*, 2003.
Fourth SIS-ECM Symposium, Phoenix, Arizona, Dec. 6-7, 2002.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Letter and Memo reporting Office Action issued in Mexican Application No. PA/a/2001/001124, mailed Jul. 13, 2004.
McCarty, "Cook Incorporated forms dedicated tissue engineered products group," *Cook® Online, News and Media Information*, 2000.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.

Office Action issued in U.S. Appl. No. 09/994,537, mailed Jun. 30, 2003.
Office Action issued in U.S. Appl. No. 10/144,504, mailed May 15, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,623, mailed Jun. 9, 2006.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 10, 2007.
Office Action issued in U.S. Appl. No. 10/524,957, mailed Aug. 3, 2009.
Office Action issued in U.S. Appl. No. 10/524,957, mailed Sep. 30, 2008.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.
Office Action issued in U.S. Appl. No. 11/230,988, mailed Oct. 3, 2008.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/684,989, mailed Jul. 7, 2009.
Office Action issued in U.S. Appl. No. 11/684,989, mailed Nov. 18, 2008.
PCT Declaration of Non-Establishment of International Search Report issued in International Application No. PCT/US2003/17099, mailed Nov. 7, 2003.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus, First Edition (v 1.3.1), 2007.
Search Report issued in Hungarian Application No. P0103545, mailed Oct. 29, 2001.

Search Report issued in Hungarian Application No. P0500055, mailed May 3, 2005.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Supplementary Search Report issued in European Application No. 08010957.2, mailed Aug. 27, 2008.
Wooding-Scott et al., "No wound is too big for resourceful nurses," *RN*, pp. 22-25, 1988.
Arnljots and Svedman, "Irrigation Treatment in Split-Thickness Skin Grafting of Intractable Leg Ulcers," *Scand J. Mast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96.
Blackburn II et al.; "Negative-pressure dressings as a bolster for skin grafts," *Annals of Plastic Surgery*, 40(5):453-457, 1998.
Chinn and Burns, "Closed wound suction drainage," *The Journal of Foot Surgery*, 24(1):76-81, 1985.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Davydov et al., "Vacuum Therapy in the Treatment of Purulent Lactation Mastitis," *Vestnik Khirurgi*, pp. 66-70 (and 9 page English translation thereof), May 1986.
Egnell Minor, Instruction Book, First Edition, 300, 7502, p. 24, Feb. 1975.
Egnell Minor: Addition to the Users Manual Concerning Overflow Protection -Concerns all Egnell Pumps, p. 2, Feb. 1983.
Greer et al., "The use of subatmospheric pressure dressing therapy to close lymphocutaneous fistulas of the groin," *British Journal of Plastic Surgery*, 53(6):484-487, 2000.
Johnson, "An improved technique for skin graft placement using a suction drain," Surgery, Gynecology, and Obstetrics, 159(6):584-585, 1984.
Kostyuchenok et al., "Vacuum treatment in the surgical management of purulent wounds"; Vestnik Khirurgi, pp. 18-21 (and 6 page English translation thereof), Sep. 1986.
Kuznetsov and Bagautdinov, "Vacuum and Vacuum-Sorption Treatment of Open Septic Wounds," in II All—Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," *Journal of Cardiovascular Surgery*, 31:634-639, 1990.
Masters, "Reliable, inexpensive and simple suction dressings," Letter to the Editor, *British Journal of Plastic Surgery*, Elsevier Science/The British Association of Plastic Surgeons, UK, 51(3):267, 1998.
Mendez-Eastman, "When wounds won't heal" *RN*, 61(1):20-24, 1998.
Meyer and V. Schmieden, *Bier's Hyperemic Treatment in Surgery, Medicine, and the Specialties: A Manual of Its Practical Application*, (W.B. Saunders Co., Philadelphia, Pa 1909), pp. 17-25, 44-64, 90-96, 167-170, and 210-211.
Office Action issued in U.S. Appl. No. 10/509,137, mailed Dec. 20, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Jan. 10, 2007.
Office Action issued in U.S. Appl. No. 10/509,137, mailed Nov. 24, 2008.
Office Action issued in U.S. Appl. No. 11/515,983, mailed May 11, 2009.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Orringer et al., "Management of wounds in patients with complex enterocutaneous fistulas," *Surgery, Gynecology & Obstetrics*, 165:79-80, 1987.
PCT International Preliminary Examination Report issued in International Application No. PCT/GB96/02802, mailed Jan. 15, 1998.
PCT International Search Report issued in International Application No. PCT/GB96/02802, mailed Apr. 29, 1997.
PCT International Search Report issued in International Application No. PCT/GB98/02713, mailed Jan. 8, 1999.
PCT International Search Report issued in International Application No. PCT/GB95/01983, mailed Nov. 23, 1995.
PCT Written Opinion issued in International Application No. PCT/GB96/02802, mailed Sep. 3, 1997.
PCT Written Opinion issued in International Application No. PCT/GB98/02713, mailed Jun. 8, 1999.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
Schein et al., "The 'Sandwich Technique' in the management of the open abdomen," *British Journal of Surgery*, 73:369-370, 1986.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary European Search Report, issued in European Application No. EP 02 79 4388, mailed Jun. 16, 2009.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Tennant, The use of hypermia in the postoperative treatment of lesions of the extremities and thorax, *Journal of the American Medical Association*, 64:1548-1549, 1915.
Tribble, "An improved sump drain—irrigation device of simple construction," *Archives of Surgery*, 105(3):511-513, 1972.
Yusupov et aL, "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and copy and certified translation), 1986.
Davydov, et al., Vestn. Khir., Sep. 1988—"Vacuum Therapy in the Treatment of Acute Suppurative Diseases of Soft Tissues and Suppurative Wounds" (English transiation by R. McElroy Trranslation Co., Austin, Texas.
Davydov, et al., Khirurgila, Jun. 1990—"Pathogenic Mechanism of the Effect of Vacuum Therapy on the Course of the Wound Process" (English translation by R. McElroy Translation Co., Austin, Texas).
Davydov, et al., Vestn. Khir., Nov. 1986—"Vacuum Therapy in the Treatment of Suppurative Lactation Mastitis" (English translation by R. McElroy Translation Co., Austin, Texas).

Davydov, et al., Vestn. Khir., Oct. 1988—"Bacterlological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the Use of Forced Early Secondary Suture in the Treatment of Suppurative Wounds" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (English translation by R. McElroy Translation Co., Austin, Texas).

Jeter, et al., Chronic Wound Care; 27: pp. 240-246—"Managing Draining Wounds and Fistulae: New and Established Methods".

Mulder, et al., Wound Healing Publications 1991—"Clinicians' Pocket Guide to Chronic Wound Repair".

Valenta, AIN Apr. 1994; pp. 44-45—"Using the Vacuum Dressing Alternative for Difficult Wounds".

Wolthuis, et al., Physiological Reviews Jul. 1974; vol. 54, No. 3, pp. 566-595—"Physiological Effects of Locally Applied Reduced Pressure in Man".

Fleischmann, WundForum Spezial IHW 1994; pp. 54-55—"Vacuum Sealing for Treatment of Problematical Wounds" (English translation provided).

Bucalo, et al., Wound Repair and Regeneration; Jul.-Sept. 1993; pp. 181-186—"Inhibition of Cell Proliferation by Chronic Wound Fluid".

Olenius, et al., Plastic and Reconstructive Surgery Feb. 1993: pp. 213-215—"Mitotic Activity in Expanded Human Skin".

Viljanto, at al., Br. J. Surg. 1976; vol. 63: pp. 427-430—"Local Hyperalimentation of Open Wounds".

Dunlop, at al., Br. J. Surg. May,1990; vol. 77: pp. 562-563—"Vacuum Drainage of Groin Wounds after Vascular Surgery: A Controlled Trial".

Comment—Dunlop et al., Apr. 1991, pp. 505-506 on "Vacuum Drainage of Groin Wounds after Vascular Surgery".

Morykwas, et al., Extracellular Matric and Healing 1993; pp. 800—"Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds"; Feb. 11, 1999; 16 pages.

Chariker, at al., Contemporary Surgery Jun. 1989; vol. 34: pp. 59-63—"Effective Management of Incisional and Cutaneous Fistulae with Closed Suction Wound Drainage".

Tittel, et al., Eingag and Annahme des Manuskripts Jan. 7, 1987; pp. 104-107—"New Standards in Postoperative Wound Drainage".

Genecov, et al., Annals of Plastic Surgery Mar. 1998; vol. 40, No. 3: pp. 219-225—"A Controlled Subatmospheric Pressure Dressing Increases the Rate of Skin Graft Donor Site Reepithelization".

Morykwas, et al., Annals of Plastic Surgery Jun. 1997; vol. 38, No. 6—"Vacuum-Assisted Closure: A New Method for Wound Control and Treatment: Animal Studies and Basic Foundation".

Argenta, et al., Annals of Plastic Surgery Jun. 1997; vol. 38, No. 6:—"Vacuum-Assisted Closure: A New Method for Wound Control and Treatment: Clinical Experience".

Nakayama, et al., Ann Plast Surg. May 1991: vol. 26, No. 5: pp. 499-502—"A New Dressing Method for Free Skin Grafting in Hands".

Nakayama, et al., Plast. Reconstr. Surg., Dec. 1990.; vol. 86, No. 6: pp. 1216-1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).

Teder, et al., J. Invest. Surg.1990; vol. 3: pp. 399-407—"Continuous Wound Irrigation in the Pig".

Wood, et al., Br. J. of Surg.1977; vol. 64: pp. 554-557—"Foam Elastomer Dressing in the Management of Open Granulating Wounds: Experience with 250 Patients".

Kostluchenok et al., Vestn. Khir. Sep. 1986— "Vacuum Treatment in the Surgical Treatment of Suppurative Wounds" (English translation by R. McElroy Translation Co., Austin, Texas).

Lundvall, et al., Acta Physiol. Scand. 1989, vol. 136: pp. 403-409—"Transmission of Externally Applied Negative Pressure to the Underlying Tissue. A Study on the Upper Arm of Man".

Brochure—KCI—The V.A.C. (Vacuum Assisted Closure), Nov. 5, 1998; 7 pages.

Brochure—Augustine Medical, Warm-Up Active Wound Therapy Wound Covers, 1999; 3 pages.

US 6,216,701, 04/2001, Heaton et al. (withdrawn)

\* cited by examiner

US 7,723,560 B2

WOUND VACUUM THERAPY DRESSING KIT

CROSS-REFERENCE TO RELATED APPLICATIONS

This application is a U.S. national counterpart application of international application Ser. No. PCT/US02/41231 filed Dec. 20, 2002, which claims the benefit of U.S. provisional application Ser. No. 60/344,620 filed Dec. 26, 2001.

BACKGROUND OF THE INVENTION

The present invention relates to wound dressing kits, and particularly to the provision of kits for use with wound vacuum systems.

The prior art contemplates kits for wound medical treatment, such as first aid kits, for example. Such kits usually include bandages for treating wounds, gauze, scissors, and/or medical tape. Conventional kits, however, are not equipped with specialized devices for treating chronic open wounds, such as decubitus ulcers.

SUMMARY OF THE INVENTION

The present invention comprises one or more of the following features discussed below, or combinations thereof:

A wound vacuum therapy dressing kit is provided for use with a wound drainage system. The contents of the kit are provided to aid a caregiver when installing or changing the vacuum bandage. The kit may include a wound dressing member having a wound contacting surface that may be configured to be in contact with and generally conform to the wound surface. The member may further include a plurality of discrete holes formed in the wound contacting surface and a port configured for communication with the vacuum source. The member may further include a passageway between each hole and the port. The kit may further include various components or accessory items that are used in conjunction with the wound dressing member.

An illustrative kit may include a sealing film for placement over the member. The sealing film may adhere to a patient's healthy skin surrounding the wound. The illustrative kit may also include a wound measurement device for measuring and recording the size of the wound at the time the caregiver changes the vacuum bandage. The wound measurement device may include a transparent top portion and a transparent bottom portion removably coupled to the top portion. The bottom portion may be placed adjacent the wound surface and the top portion may be folded for placement adjacent the bottom portion. The top portion may include a drawing surface and a grid coupled to the drawing surface on which the caregiver may draw or trace the size of the wound for keeping with the patient's records, for example.

A kit in accordance with this disclosure may further include a tube guide that may be coupled to the healthy skin surrounding the patient's wound. The tube guide may have an aperture for receiving and positioning a vacuum tube coupled to the member and to a vacuum source. The tube guide may include a curved upper surface for contact with the sealing film. When the bandage is assembled, the film may be draped over the upper surface of the tube guide to couple with the upper surface of the tube guide and effect a seal around the tube guide. The tube guide may further include a flat bottom surface and an adhesive layer coupled to the bottom surface. The adhesive layer may couple the bottom surface of the guide to the patient's healthy skin surrounding the wound.

The guide may further include an opening through a side wall into the aperture, which opening may be defined by confronting first and second surfaces. The opening of the guide may be in communication with the aperture. The first surface and the second surface may be generally parallel to each other and may be inclined with respect to the bottom surface. The tube may be placed within the aperture by moving the first surface and second surface away from each other and passing the tube through the opening for placement within the aperture. The sealing film draped over the guide may effectively cause the first surface to abut the second surface thus sealing the opening.

The kit may further include a patch sheet. The patch sheet may include a first layer and a second layer releasably coupled to the first layer. The second layer may include an adhesive and may be die cut to form circular patches and rectangular strips. The patches and strips may be used with the sealing film to repair and seal any leaks, tears, or holes, for example, to provide a sealed environment about the wound and create a vacuum space above the wound.

It will be appreciated that the kit may also include a variety of components such as those shown and described in the disclosures of the patent applications, patent publications, and issued patents incorporated by reference herein including vents, venting lines, valves, stopcocks, multi-lumen tubes and tubing sets, wound inserts, wound packing, and external catheter access collars, for example.

Features of the disclosure will become apparent to those skilled in the art upon consideration of the following detailed description of the preferred embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION OF THE DRAWINGS

Figure 1:
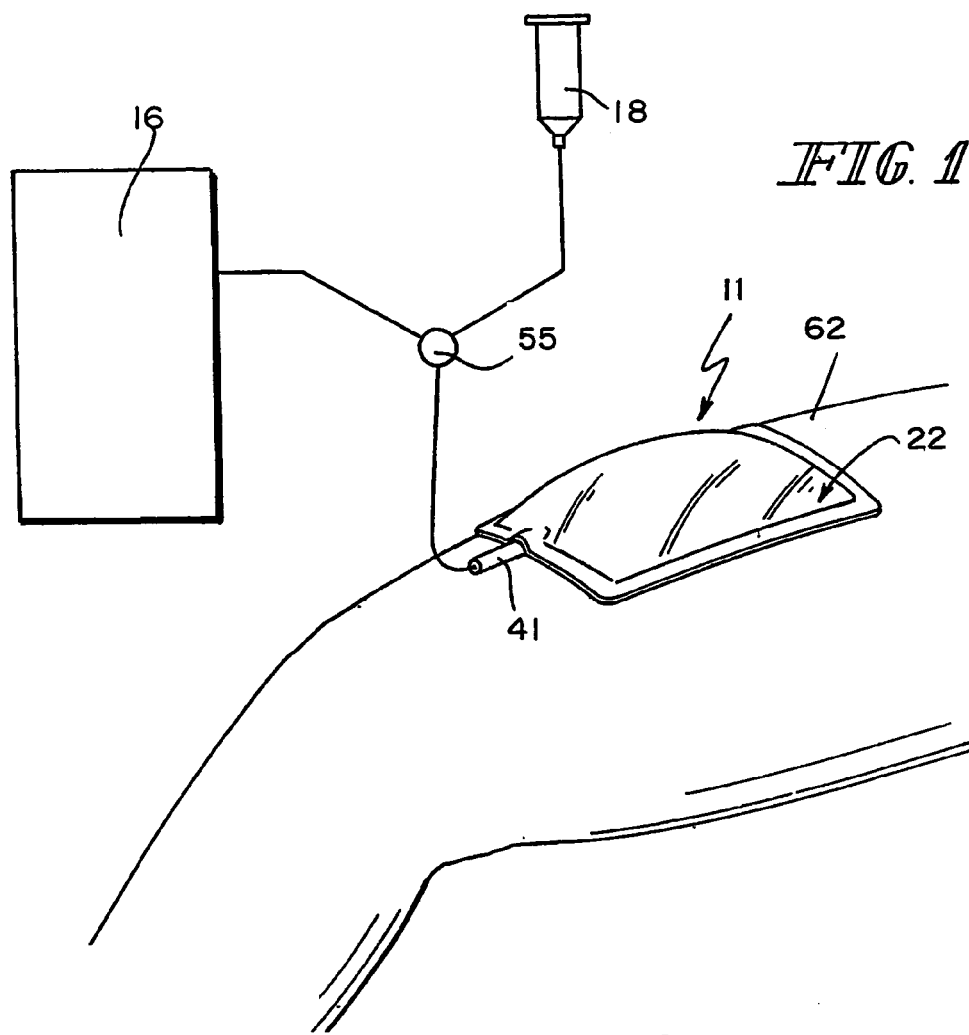
FIG. 1 is a part perspective, part diagrammatic view of a wound care bandage showing the wound care bandage located on the leg of a patient and coupled to both a vacuum source and an irrigation source through the use of a switch valve.
Figure 2:
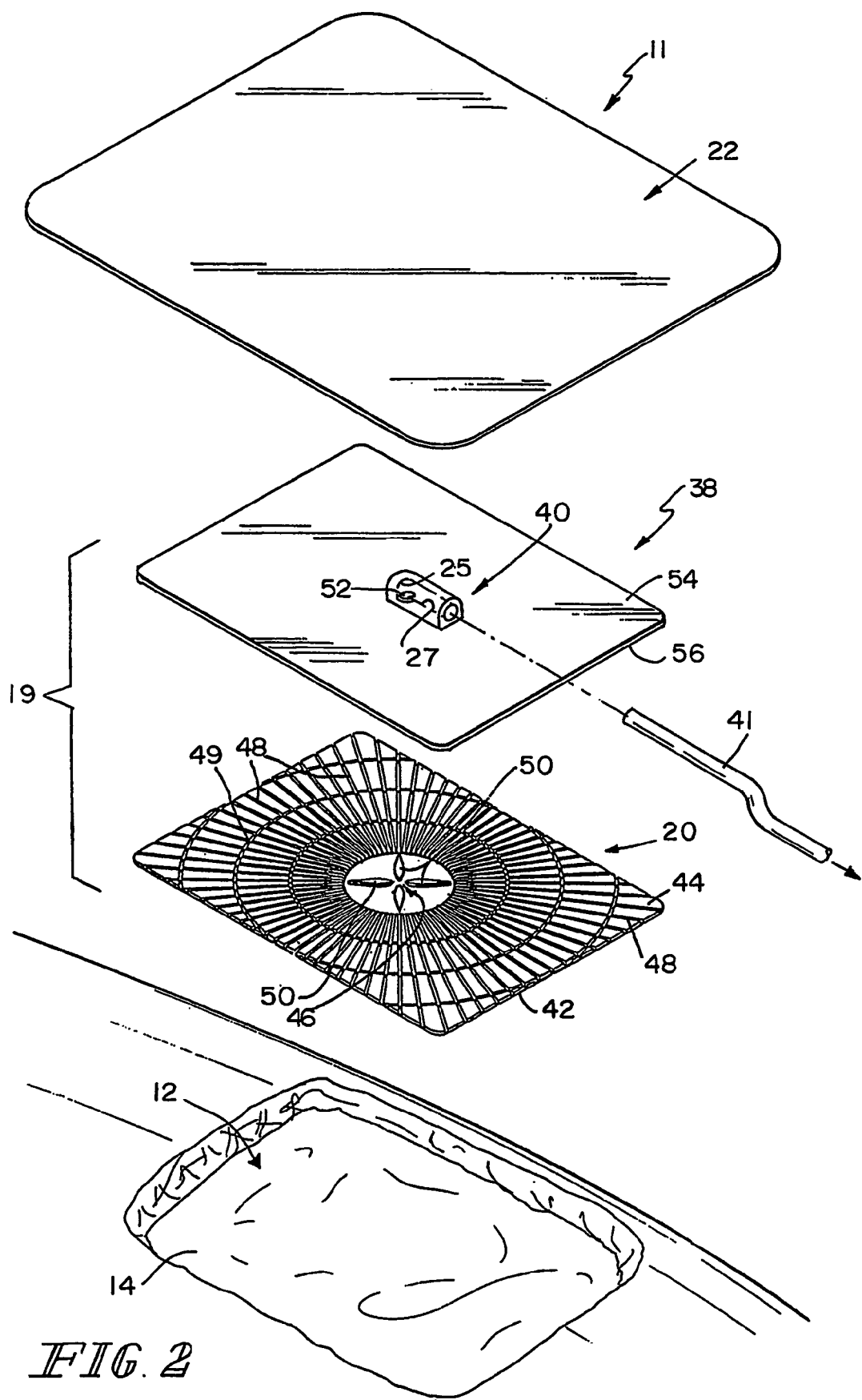
FIG. 2 is an exploded perspective view of the wound care bandage positioned above a wound bed showing a wound contacting layer and a cover of the bandage which cooperate to form a wound dressing member for placement within the wound bed, and also showing a sealing film to cover the member and seal about the wound.
Figures 5, 6:
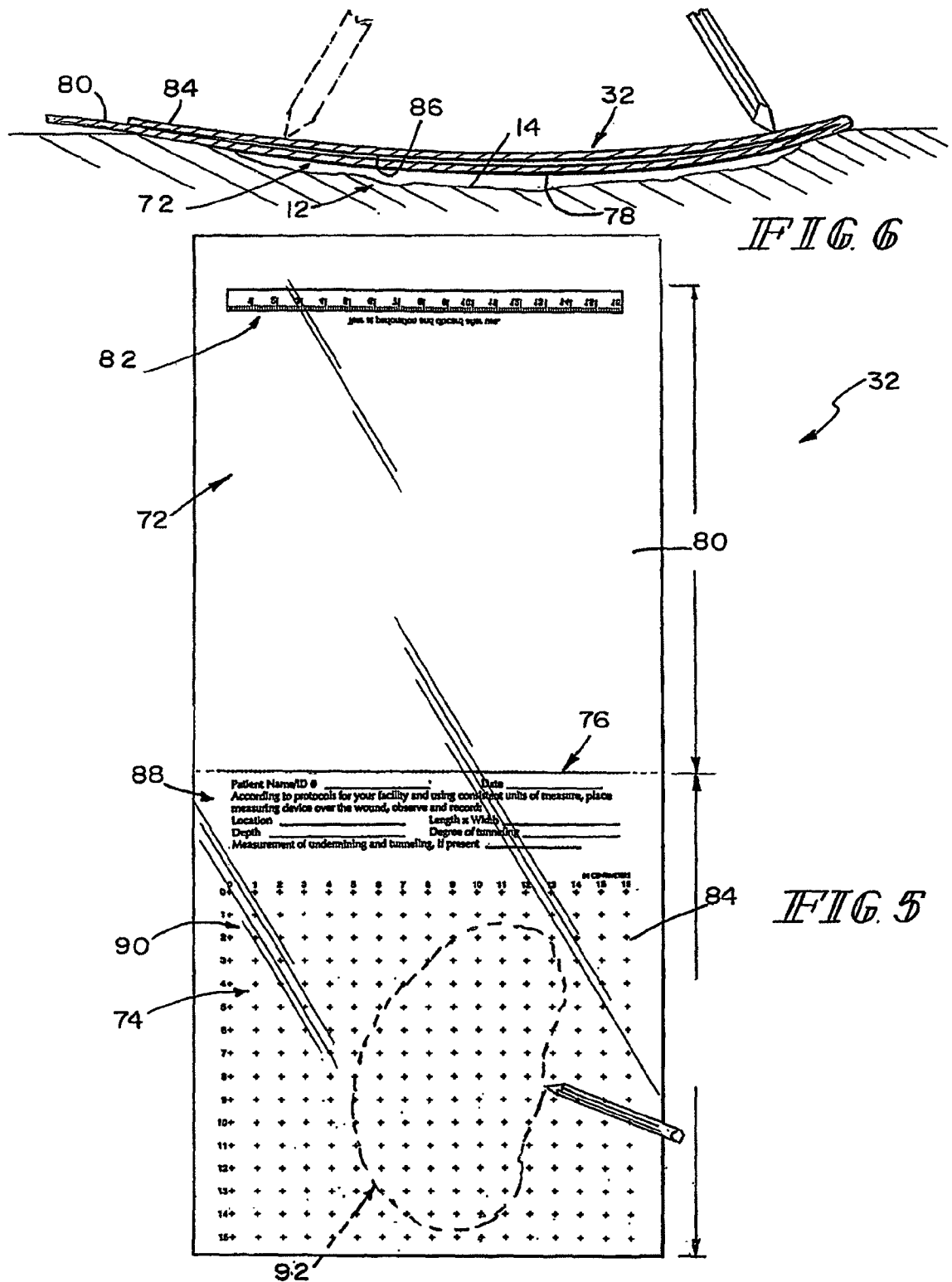
FIG. 5 is a top plan view of the wound measurement device.
FIG. 6 is a sectional view of the wound measurement device of the kit showing the wound measurement device adjacent a wound for measuring the size of the wound by tracing an outline of the wound onto the device.

A wound vacuum therapy dressing kit 10 is provided for applying or changing a vacuum dressing or bandage 11 that is used for treatment of a chronic open wound 12 having a wound surface 14, such as that shown in FIGS. 2 and 6, for example. Generally, bandage 11 includes a wound dressing member 19 that is placed on the wound surface 14 and a sealing film 22 to cover the member 19 and seal about the wound 12 to create a vacuum space above the wound 12. Member 19 is configured for communication with a vacuum source 16 and optionally an irrigation source 18, as shown in FIG. 1. The bandage 11 and vacuum source 16 make up a wound drainage system. It is also within this disclosure to include a wound drainage system having irrigation source 18, although irrigation source 18 is not required.

Bandage 11 promotes the healing of wound 12 by providing vacuum therapy to wound 12 to promote blood flow and remove exudate from wound surface 14 and by providing for irrigation of the wound with fluids such as saline, for example. An illustrative wound treatment apparatus having a wound temperature control system, a medicine delivery system, and a drainage system is disclosed in U.S. Pat. No. 6,458,109. An illustrative vacuum and irrigation system is disclosed in U.S. Patent Publication No. US 2002/0161317 A1. Additionally, an illustrative vacuum bandage is disclosed in U.S. Pat. No. 6,685,681. Alternative vacuum bandages are disclosed in U.S. Patent Publication No. US 2002/0082567 A1. Further, a vacuum bandage system including a controller of the system is disclosed in U.S. Patent Application Publication No. US 2002-0198504A1, titled WOUND TREATMENT APPARATUS and in U.S. Patent Application Publication No. US 2002-0198503 A1,titled WOUND TREATMENT APPARATUS. All of these publications and patents are hereby incorporated herein by reference.

Figure 4:
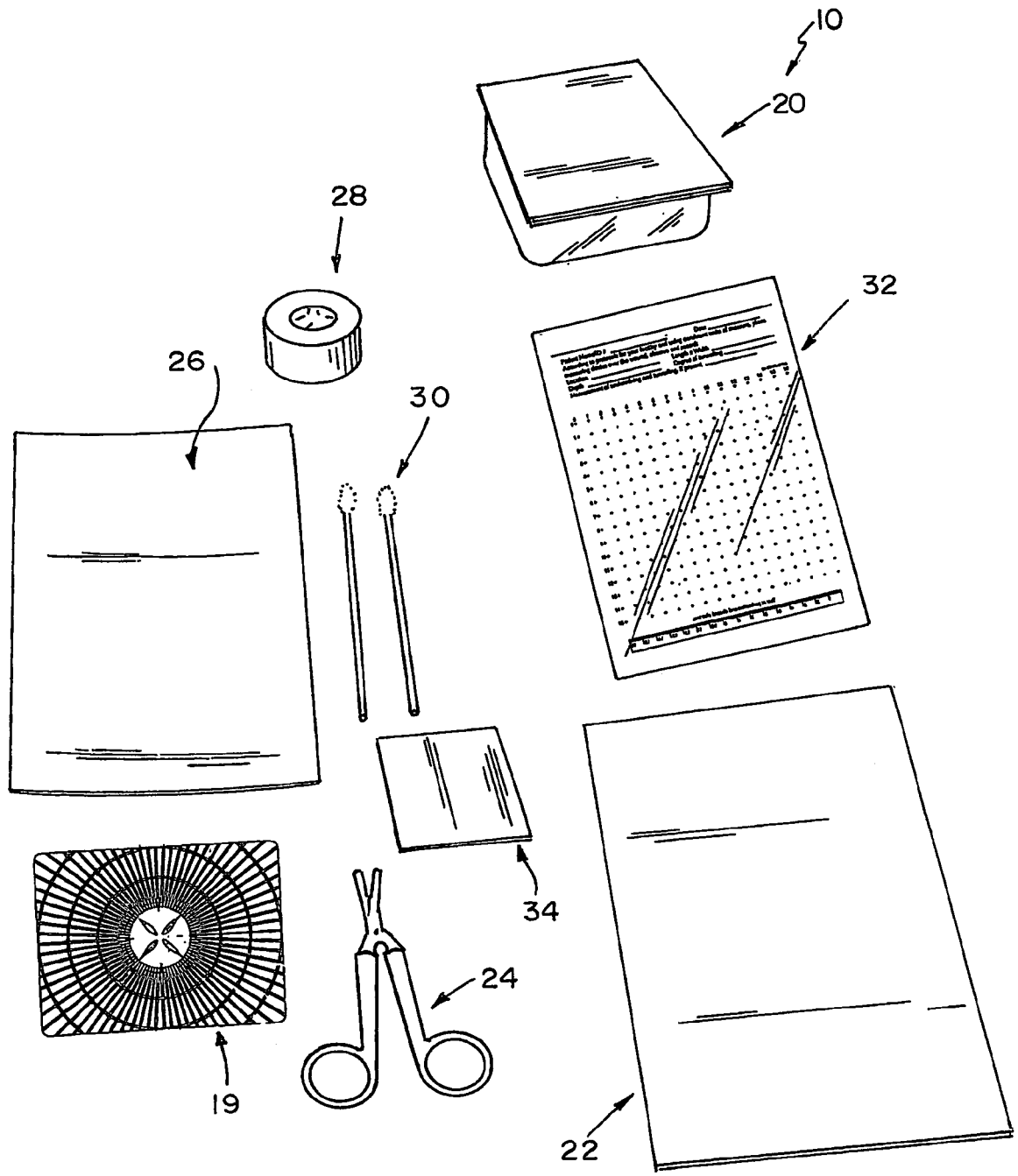
FIG. 4 is a perspective view showing components of one example of a kit including a pair of pre-packaged gloves, scissors, two cotton-tipped applicators, a wound measurement device, pre-packaged gauze, hypo-allergenic tape, a skin protectant, a sealing film, and the thin, flexible wound dressing member of FIGS. 1-3.

Optionally, a packing material such as gauze 20 shown in FIG. 4, for example, is provided for placement over the member 19 and under film 22. It will be appreciated, however, that some caregivers may choose to leave the gauze 20 out of the bandage 11 and place the sealing film 22 directly over and in direct contact with member 19 to seal to the patient's healthy skin 62 surrounding the wound 12. Further, it will be appreciated that gauze 20 may be used to serve functions other than packing. For example, gauze 20 may be used to absorb excess liquid from the wound surface 14 prior to placing member 19 onto wound surface 14. It will be appreciated that a variety of other materials may be used as packing.

Vacuum bandages 11 are changed from time to time by caregivers. For example, as a patient's wound heals and becomes smaller, one bandage 11 is removed and a new, smaller bandage 11 is applied. Wound vacuum therapy dressing changes often require many medical supplies that a caregiver has conventionally sourced separately. Kit 10 contains all, or substantially all, of the necessary supplies or accessory items for applying or changing a vacuum wound therapy bandage in one package, thus relieving the caregiver of the time and expense associated with ordering, stocking, and locating each of these items separately. Thus, kit 10 increases productivity of the caregiver.

In one embodiment, kit 10 includes member 19, gauze 20 such as KERLIX™ non-linting gauze by Kendall, sealing film 22 such as 3M's TEGADERM® brand sealing film, scissors 24, a pair of pre-packaged gloves 26, hypo-allergenic tape 28 such as DERMIVIEW® brand tape made by Johnson & Johnson, two sterile cotton swabs 30, a wound measurement device 32, and a skin protectant 34, as shown in FIG. 4. Although each component of kit 10 is disclosed above with respect to a certain brand, it is within the scope of this disclosure to include any brand or type of the above-mentioned products. For example, OPSITE FLEXIGRID® semipermeable dressing made by Smith & Nephew may be used in lieu of TEGADERM® sealing film in some embodiments.

Figure 3:
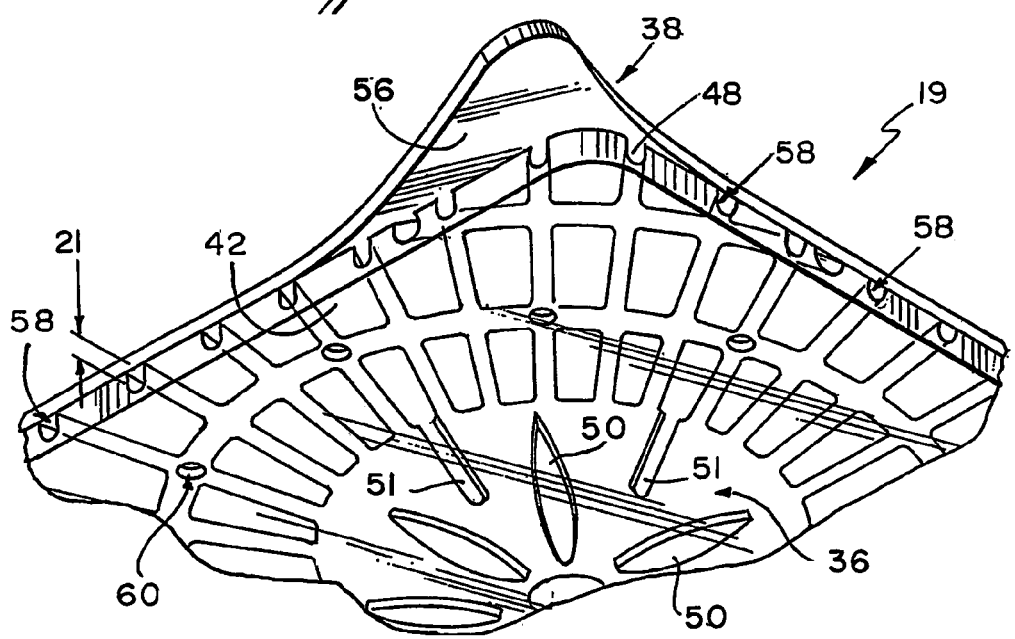
FIG. 3 is a bottom perspective view of a portion of the member provided in a wound vacuum therapy dressing kit in accordance with this disclosure showing a smooth wound contacting surface of the member and also showing the transparent nature of the member.

Member 19, as shown in more detail in FIGS. 2 and 3, is made of non-porous, non-adhesive, and generally non-compressible silicone. Vacuum source 16 acts to remove exudate by creating a negative pressure above the wound surface 14 which draws the exudate up through member 19. Irrigation source 18 acts to irrigate the wound surface 14 by supplying a fluid for flushing through member 19 onto wound surface 14. Member 19 is substantially transparent and has a rectangular shape, as shown in FIGS. 2-4. However, it is within the scope of this disclosure to include in kit 10 one or more members having other suitable shapes. Thus, the wound dressing members of the kit 10 may have a variety of sizes, configurations and durometers or degrees of softness and may be configured to conform to different portions of a patient's body such as the heel, sternum, elbow, etc. Examples of some alternative wound dressing members are shown in U.S. Pat. No. 6,685,681, and U.S. Patent Application Nos. US 2002/082567 A1, and US 2002/0161346 A1,the disclosures of which are hereby incorporated by reference herein. Yet another illustrative wound dressing members is disclosed in PCT International Publication No. WO 03/086232; which was filed concurrently herewith; which is titled ACCESS OPENINGS IN VACUUM BANDAGE which is hereby incorporated by reference herein.

Illustrative member 19, shown in FIGS. 2-4, includes a wound contacting layer 36 and a cover 38 coupled to layer 36. Member 19 also includes a connector 40 coupled to cover 38 for communication with vacuum source 16 and/or irrigation source 18 via a tube 41. Layer 36, cover 38, and connector 40 are each made of a medical grade silicone or other type of pliable elastomer. Two companies, for example, which manufacture such medical grade silicone are GE Silicones and NuSil Technology. It is within the scope of this disclosure, however, to include a member made of any type of thin, flexible material which is illustratively non-porous and non-foam-like. This thin, flexible material is also illustratively generally non-absorptive. For example, materials such as polyvinylchloride (PVC), PVC free of diethylhexyl phthalate (DEHP-free PVC), polyurethane, or polyethylene may be used in the manufacture of member 19. Further, layer 36, cover 38, and connector 40 may each be molded to include anti-microbial constituents. For example, it is within the scope of this disclosure to impregnate member 19 with silver ions which are known anti-microbials.

Member 19, including layer 36, cover 38, and connector 40, is also made of a generally non-adhesive material. Therefore, layer 38, which lies adjacent to wound surface 14, does not adhere to wound surface 14. Further, member 19 is solid in nature and generally non-compressible. For example, when a negative pressure is applied to member, 19, a thickness, 21, of member 19, as shown in FIG. 3, remains relatively constant. Further, as shown in FIG. 3, member 19 is substantially transparent. Therefore, a caregiver or user is able to see the wound 12 through member 19 when member 19 is placed adjacent to wound surface 14. This transparency allows the caregiver to view the progress of the healing of wound 12.

Layer 36 includes a wound contacting surface 42 and an upper or opposite surface 44. Wound contacting surface 42, or portions thereof, contacts and generally conforms to the wound surface 14. Opposite surface 44 includes a central area 46 and a plurality of channels 48 extending radially away from central area 46. Concentric channels 49 are also formed in layer 36, as shown in FIGS. 2 and 3. Central area 46 is recessed relative to the portions of upper surface 44 between channels 48, 49 as shown in FIG. 2. Channels 48 are open at the sides and ends of member 19. Illustratively, each channel 48, 49 is 0.030 inch (0.762 mm) wide and 0.030 inch (0.762 mm) deep. It is within the scope of this disclosure, however, to include channels 48, 49 of opposite surface 44 having various widths and depths suitable for the present application. As shown in FIG. 2, central area 46 of layer 36 is provided to communicate with the vacuum source 16 and irrigation source 18 through cover 38, as will be described below.

A plurality of radially extending protrusions or bosses 50 are positioned around central area 46. Bosses 50 are positioned between central area 46 and channels 48, 49, as shown in FIG. 2. Bosses 50 prevent central area 46 from collapsing in on a port 52 of cover 38 and forming an unwanted seal which would effectively block air flow through port 52 while suction is applied to bandage 11. Port 52 communicates with the vacuum source 16 and/or the irrigation source 18 via connecter 40 and tube 41, as shown in FIGS. 1 and 2. As mentioned above, port 52 is in communication with central area 46 of layer 36. Illustratively, four bosses 50 are shown in FIG. 2. However, it is within the scope of this disclosure to provide any number of bosses 50 or the like in central area 46 of layer 36 to prevent central area 46 from sealing off port 52 of cover 38 suction is applied to bandage 11. Further, it is within the scope of this disclosure to include bosses 50 having a tapered cross-section, for example, or to include a boss or bosses having any shape that prevents central area 46 from sealing off port 52 when suction is applied to bandage 11. Alternative or supplemental bosses 51 are shown in FIG. 3. Bosses 51 are positioned between bosses 50 and further prevent central area 46 collapsing on port 52 and forming an unwanted seal blocking air flow through port 52 while suction is applied to bandage 11. Alternative bosses are generally rectangularly shaped and extend inwardly from channels 48 toward port 52.

Connecter 40, as shown in FIG. 2, is a tubal port coupled to a top surface 54 of cover 38 and in communication with port 52 of cover 38. As mentioned before, it is within the scope of this disclosure for connecter 23 to be a separate component of member 19 which is coupled to cover 38 or for connecter 23 to be molded integrally with cover 38. Connector 40 includes a passageway formed at a right-angle. Thus, the passageway in connector 40 has a vertical portion 25 that communicates with port 52 and a horizontal portion 27 that communicates with vertical portion 25. Connector 40 connects with tube 41 to provide a horizontal tube attachment with respect to port 52. Cover 38 further includes a bottom surface 56. Bottom surface 56 engages opposite surface 44 of layer 36, as shown in FIG. 3.

As mentioned above, cover 38 is coupled to layer 36 and connecter 40 is coupled to cover 38 to form member 19. Cover 38 and layer 36 cooperate to form distinct passageways 58 of member 19 defined by channels 48, 49 of layer 36 and bottom surface 56 of cover 38. Passageways 58 are in communication with central area 46 of layer 36 and central area 46 of layer 36 is in communication with port 52 of cover 38 which is in communication with the vacuum and/or irrigation sources 16, 18 via connecter 40 and tube 41. Therefore, passageways 58 are in communication with the vacuum and/or irrigation sources 16, 18.

Member 19 includes through holes 60 which extend from channels 48, 49 through layer 36 to wound contacting surface 42, as shown in FIG. 3. Holes 60 are distinct and are provided to communicate with channels 48, 49 of layer 36. Holes 60 therefore communicate with passageways 58 of member 19 and the vacuum and/or irrigation sources 16, 18 as well to allow the suction from the vacuum source 16 and/or the fluid from the irrigation source 18 to reach the wound surface 14 via the holes 60. As shown in FIG. 3, holes 60 have a staggered arrangement. Illustratively, holes 46 are 0.020 inch (0.508 mm) in diameter and are spaced approximately 0.500 (12.700 mm) apart along channels 48, 49 of layer 36. It is, however, within the scope of the disclosure to include holes having other suitable sized diameters and/or other suitable spacing that allow for the removal of exudate without clogging.

Member 19 includes a smooth wound contacting surface 42, as shown in FIG. 3. Wound contacting surface 42 may also be textured or roughened. By providing member 19 with a textured or roughened surface, a space is created between surface 42 of layer 36 and wound surface 14. Through holes 60 communicate with this space which permits vacuum source 16 to establish a generally uniformly distributed vacuum or negative pressure to the wound surface 14 to draw blood from the body to the wound surface 14 and to draw exudate from the wound 12 through holes 60, into channels 48, 49 and passageways 58, and out port 52 of cover 38. It is within the scope of this disclosure to include other means for providing a space between surface 42 and wound surface 14 such as providing ribs, protrusions, channels, spacers, etc.

As mentioned above, port 52 of cover 38 communicates with vacuum source 16 and/or irrigation source 18 via connecter 40 and tube 41. As shown in FIG. 1, a switch valve 55 is provided which allows the caregiver to switch between the use of the vacuum source 16 and the irrigation source 18. It will be appreciated that a mechanism other than the switch valve 55 maybe used selectively to couple the vacuum source 16 or the irrigation source 18 to the bandage. Simple tube clamps, for example, may be used selectively to open and close the tube set provided with bandage 11. When valve 55 is switched to operate the vacuum source 16, the vacuum suction draws exudate up through holes 60 and radially inwardly through passageways 58 toward port 52 and finally through connecter 40 and tube 41. Although illustrative bandage 11 includes one central port 52, it is within the scope of this disclosure to include multiple ports. It is further within the scope of this disclosure to provide an alternative member having multiple ports and multiple passageway sets for use independent of each other.

Figure 9:
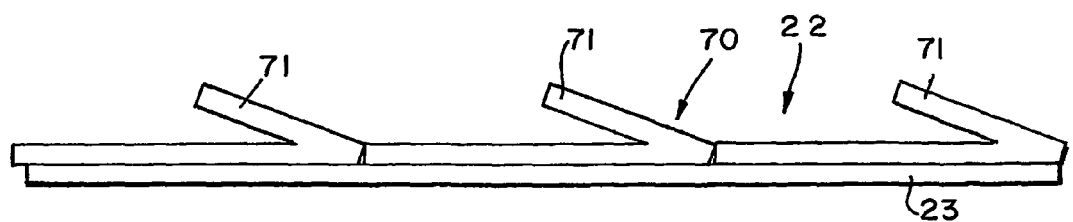
FIG. 9 is a side elevation view of the sealing film of the kit showing the sealing film including an adhesive backing for covering the wound and showing the film including release liners which are progressively removable to expose the adhesive.

As mentioned above, bandage 11 and kit 10 each further includes a sealing layer or film 22 that is placed over cover 38 and around tube 41, as shown in FIG. 1. Film 22 covers the entire wound 12 and extends across and attaches to the patient's healthy skin 62, also as shown in FIG. 1. Preferably, film 22 is an occlusive or semi-occlusive material which allows moisture to permeate through. Because of this characteristic, the film 22 is referred to as Moisture Vapor Transmission Rate film or MVTR film. As mentioned above, the products TEGADERM® made by 3M Corporation and OPSITE FLEXGRID® made by Smith and Nephew can be used for film 50, for example. The product OpSite™ is a semi-permeable film. Film 22 is approximately 0.003 inch (0.076 mm) thick. However, it is within the scope of this disclosure to include any occlusive or semi-occlusive film 22 having another thickness. Film 22 is provided to create a sealed environment below the film 22 and around the wound 12 in which a vacuum or negative pressure can be maintained as provided by vacuum source 16. As shown in FIG. 9, film 22 includes an adhesive layer 23 and release liners 70 coupled to adhesive layer 23. Illustratively, layer 23 is an adhesive backed polyurethane film. Release liners 70 include a flap 71 to be grasped by the caregiver to remove each release liner 70 and progressively expose the adhesive below for attachment of adhesive layer 23 to the patient's healthy skin 62 surrounding the wound 12.

Illustrative skin protectant 34 of kit 10 is CAVILON™ No-Sting Barrier available from 3M Corporation. Other manufactures includes BARD® Incontinence Protective Barrier Film by Bard Medical Division and NO-STING SKIN-PREP™ Protective Dressing by Smith & Nephew, for example. Skin protectant 34 is also referred to as skin barrier film. Skin protectant 34 is typically applied as a liquid that is sprayed, swabbed or wiped on the patient's healthy skin 62 with an impregnated gauze. The liquid is typically polymeric and is allowed to dry on the skin 62 to form a tin film that protects the healthy skin 62 from such things as urine and/or fecal incontinence, digestive juices, wound drainage, adhesives and friction, for example. Skin protectant 34 is also provided in kit 10 for the purpose of preventing the vacuum and irrigation tubing 41 from creating a pressure sore on the patient's healthy skin 62. It is within the scope of this disclosure for kit 10 to include suitable skin protectants other than those listed above.

Illustrative sterile cotton swabs or applicators 30 are provided on a 6-inch (15.24 cm) wooden stick and are used for measuring the depth of the wound 12 for recordation in a patient's logbook, for example, to chart the progress of the healing of the wound 12. Although two applicators 30 are provided, only one applicator 30 is required for measuring the depth of wound 12. An extra applicator is provided if needed by the caregiver. To measure the depth of wound 12, a caregiver inserts applicator 30 perpendicularly into wound 12 relative to the healthy skin surrounding wound 12. Caregiver then either grasps the wood stick or shaft portion of the applicator 30 with his/her fingers or simply marks the shaft with a pen or marker to indicate the depth of the wound 12. Using a ruler or other measuring device, the caregiver then measures the distance on the applicator 30 between the cotton tip and their finger or mark to determine a numerical value for the depth of wound 12 for recording in the patient's log book or records.

Illustrative wound tracing guide or wound measurement device 32, shown in FIGS. 1-3 is a transparent plastic film that is placed over the wound 12. Device 32 includes a a first (e.g., top) sheet or portion 74, and a second (e.g., bottom) sheet or portion 72 configured to be pulled from first or top portion 74 (e.g., by way of a perforated line 76 separating bottom portion 72 from top portion 74). Bottom portion 72 is transparent and includes a wound contacting surface 78 and an opposite surface 80 which contacts top portion 74 when device 32 is folded along perforated line 76, as shown in FIG. 6. Bottom portion 72 has a ruler 82 printed or otherwise provided thereon, as shown in FIG. 5. Illustrative ruler 82 is graduated in centimeters for measurement of the length and/or width of wound 12.

Top portion 74 of device 32 includes a drawing surface 84 and an opposite surface 86 for contact with opposite surface 80 of bottom portion 72 when device 32 is folded along the perforated line 76. Top portion 74 further includes an information recording area 88 for a caregiver to record such information as the patient's name or identification number, the date, the location of the wound 12 on the patient, the length and width of the wound 12, the depth of the wound 12 including any amount of tunneling of the wound 12, and a measurement of any undermining of the wound 12 which may be present. A grid 90 is also printed or otherwise provided on top layer 74 of device 32. Grid 90, similar to ruler 82, is calibrated in centimeters.

In use, device 32 is placed on or over wound surface 14 of wound 12 when the vacuum bandage 11 is being changed by a caregiver. That is, device 32 is place upon the wound surface 14 once sealing film 22, member 19, and gauze 20 (if used) have been removed from the wound 12 and before application of a new bandage 11 to wound 12. Device 32 is positioned so that the wound contacting surface 78 of bottom layer 72 is above and generally adjacent wound surface 14 and the patient's healthy skin 62 surrounding wound 12. Device 32 is next folded along perforated line 76 to place opposite surface 86 of top layer 74 adjacent opposite surface 80 of bottom layer 72. A caregiver then traces the shape of wound 12 (i.e. the boundary between healthy skin and wound 12) onto grid 90 of drawing surface 84 of top layer 74, as shown for example in FIG. 7 by wound outline 92. Once the outline 92 of wound 12 has been traced, device 32 is torn (e.g., by pulling second or bottom portion 72 away from first or top portion 74) along perforated line 76. Bottom portion 72, which has been in contact with wound surface 14, is discarded. Top layer 74 is maintained in the patient's log or records to record the progress and healing of wound 12 for future reference. Thus, bottom layer 72 prevents exudate, bacteria, etc. from wound 12 from contacting top layer 74.

Kit 10 further includes an alternate means of measuring the size of the patient's wound 12. As stated above, wound measurement device 32 is provided to record the wound size for the patient's records. In an alternate embodiment, member 19 includes a removable, peel-off plastic backing (not shown). It is within the discretion of the caregiver to cut or trim member 19 to fit the size of the wound 12. Therefore, when member 19 is cut to fit the size of the wound 12, the backing is trimmed as well. This backing is then removed from the member 19 and filed with the patient's records to record the size of the wound 12. It is within the scope of this disclosure for the backing to include an adhesive to stick to a sheet of paper within the patient's records, for example.

Kit 10 includes yet another means for recording the size of the wound 12. For example, member 19 could be silk-screened with dimensional markings. When member 19 is trimmed or cut to fit the wound 12 of the patient, the remaining silk-screened marking on member 19 will indicate the size of the wound 12 without the need for the caregiver to directly measure the size of the wound 12.

In order to accommodate different sized wounds 12, member 19 may be trimmed to fit a particular wound 12. Scissors 24 of kit 10 are used by a caregiver to trim member 19 to fit a particular wound 12. Another member, for example, shown in U.S. Patent Publication No. US 2002/0082567 A1 and incorporated by reference herein, includes scale markings for indicating areas where a user may trim member 19 to fit a particular wound 12. In one embodiment, the scale markings denote measurement sizes, for example, to permit a user to cut the member 19, using scissors 24, to fit a pre-measured wound 12. As mentioned above, the wound measurement device 32 is used to measure the size of the wound 12.

Tape 28 of kit 10 is used at the discretion of the caregiver to help seal film 22 to the patient's healthy skin 62 and/or to help secure tube 41 in place to prevent tube 41 from becoming disengaged from bandage 11, for example. Illustratively, tape 28 is hypo-allergenic.

Figures 7, 8:
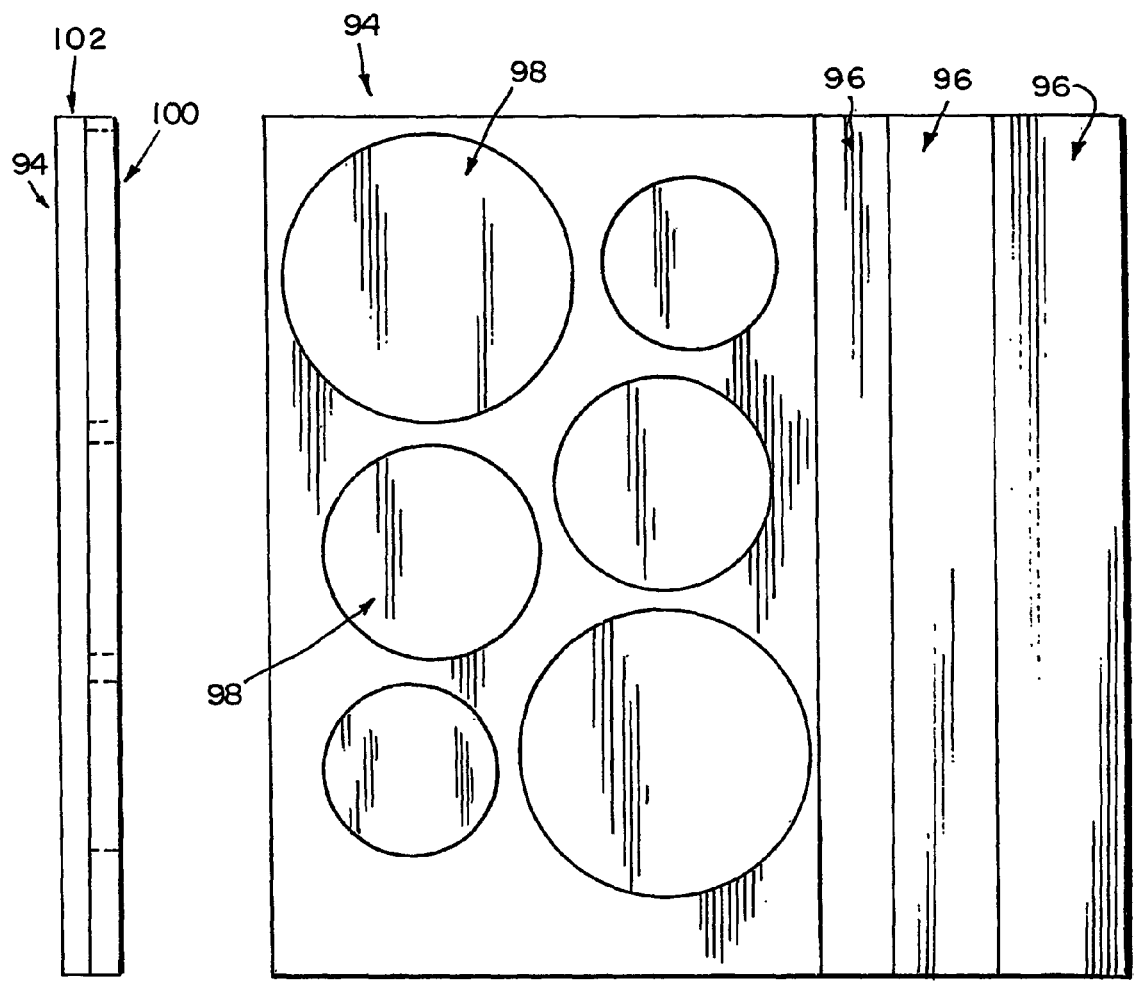
FIG. 7 is a top plan view of a patch sheet of the kit showing an adhesive layer of the sheet that is die-cut into rectangular strips and circular patches to be used to repair any leaks that occur during the course of treatment.
FIG. 8 is a side elevation view of the patch sheet of FIG. 7.

A patch sheet 94 of kit 10 is shown in FIGS. 7 and 8. Patch sheet 94 is an occlusive or semi-occlusive transparent film dressing, similar to sealing film 22, that is die-cut into strips 96 and patches 98, as shown in FIG. 7. These strips 96 and patches 98 are used by the caregiver to repair any unwanted leaks that may develop in film 22 during the course of treatment.

Patch sheet 94 is made of the same material as sealing film 22 and includes a first adhesive backed polyurethane layer 100 and a second layer 102 removably coupled to first layer 100. As shown in FIG. 7, first layer 100 is die-cut into patches 98 and strips 96 which are coupled to second layer or release liner 102. Release liner 102 is removed to expose an adhesive surface of layer 100. As shown in FIG. 9, patches 98 are circular and are shown in various sizes having ½ inch (12.7 mm), ¾ inch (19.05 mm), and 1 inch (2.54 cm) diameters, for example. Further, strips 96 are shown in various sizes having ½ inch (12.7 mm), ¾ inch (19.05 mm), and 1 inch (2.54 cm) widths. The entire illustrative patch sheet 94 is 6 inches (15.24 cm) by 6 inches (15.24 cm). It is within the scope of this disclosure, however, to include patches and strips of any suitable size and shape for repairing unwanted leaks of the sealing film 22 which occur. It is further within the scope of this disclosure for strips 96 and patches 98 to be dispensed on a roll.

In alternative embodiments, kit 10 further includes one or more of the following: a sterile mask, a gown, or other infection control garments (not shown). The sterile mask, gown, and other garments are worn by the caregiver to help maintain a clean environment and to prevent infection of the wound 12. In another alternative embodiment, kit 10 includes a wound cleanser (not shown) for cleaning wound 12 prior to prior to dressing wound 12 with bandage 11. Current wound cleansers available include Dermal Wound Cleanser by Smith & Nephew, CARRAKLENZ™ by Carrington Laboratories, Inc., and DermalHealth Wound Cleanser by Dumex Medical. It is within the scope of this disclosure, however, to include a kit 10 having other suitable wound cleansers for cleansing and disinfecting the wound surface 14.

Figure 10:
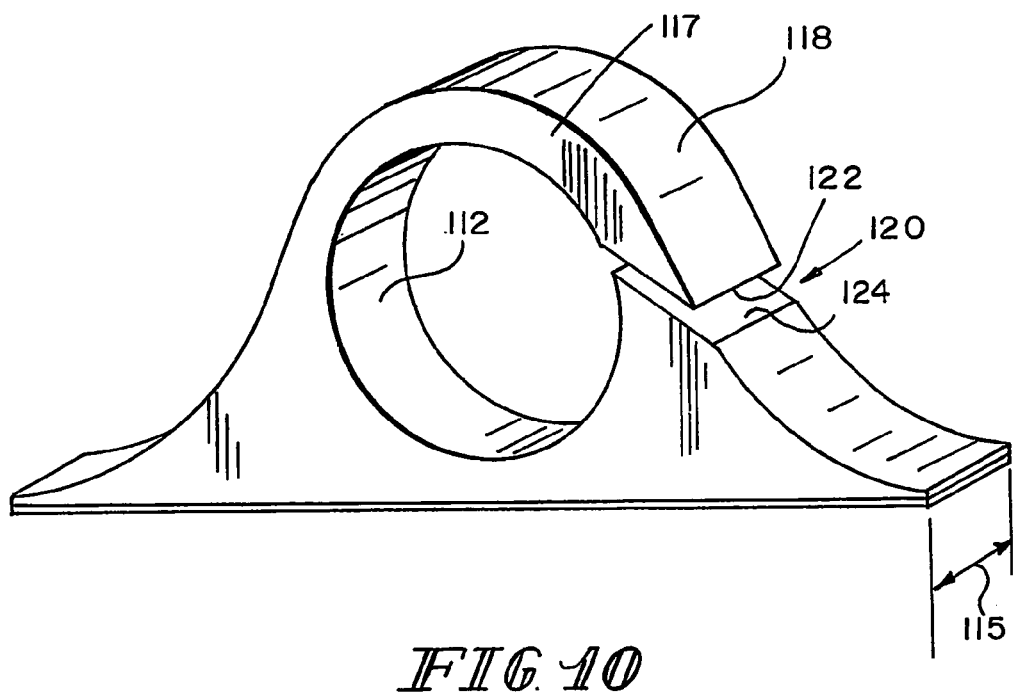
FIG. 10 is a perspective view of a tube guide which is included in some kits and which is configured for adhering to the healthy skin of the patient surrounding the wound and showing the tube guide having an opening that receives a tube which extends between the wound dressing member and the vacuum and/or irrigation source.
Figure 11:
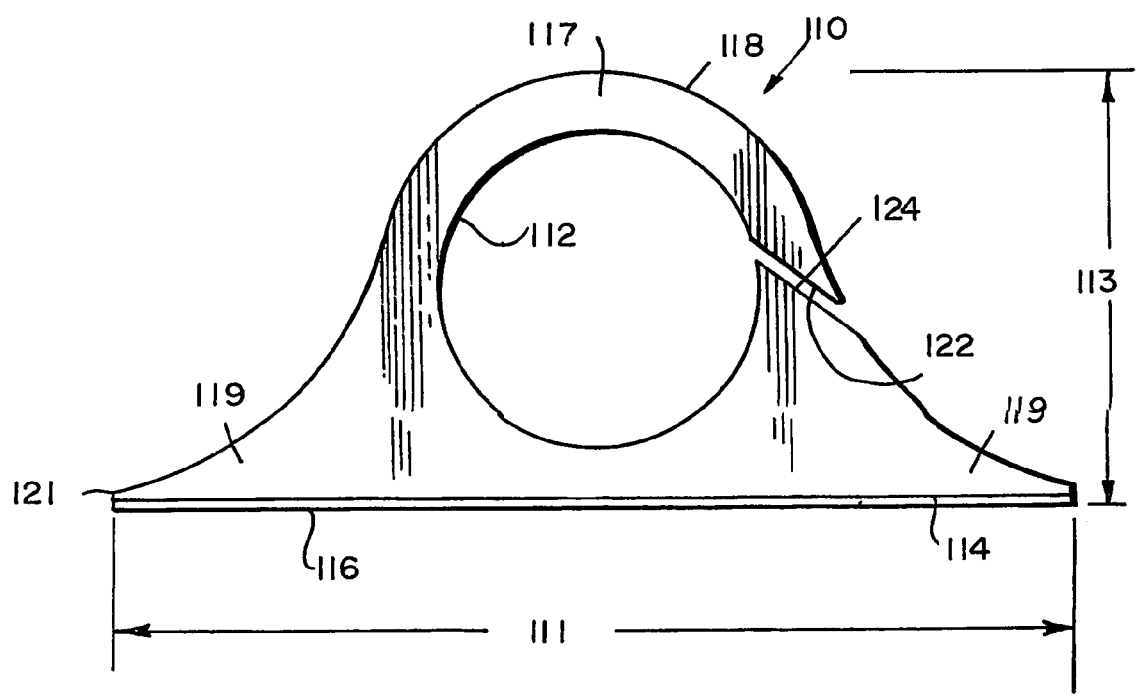
FIG. 11 is a front elevation view of the tube guide shown in FIG. 10.
Figure 12:
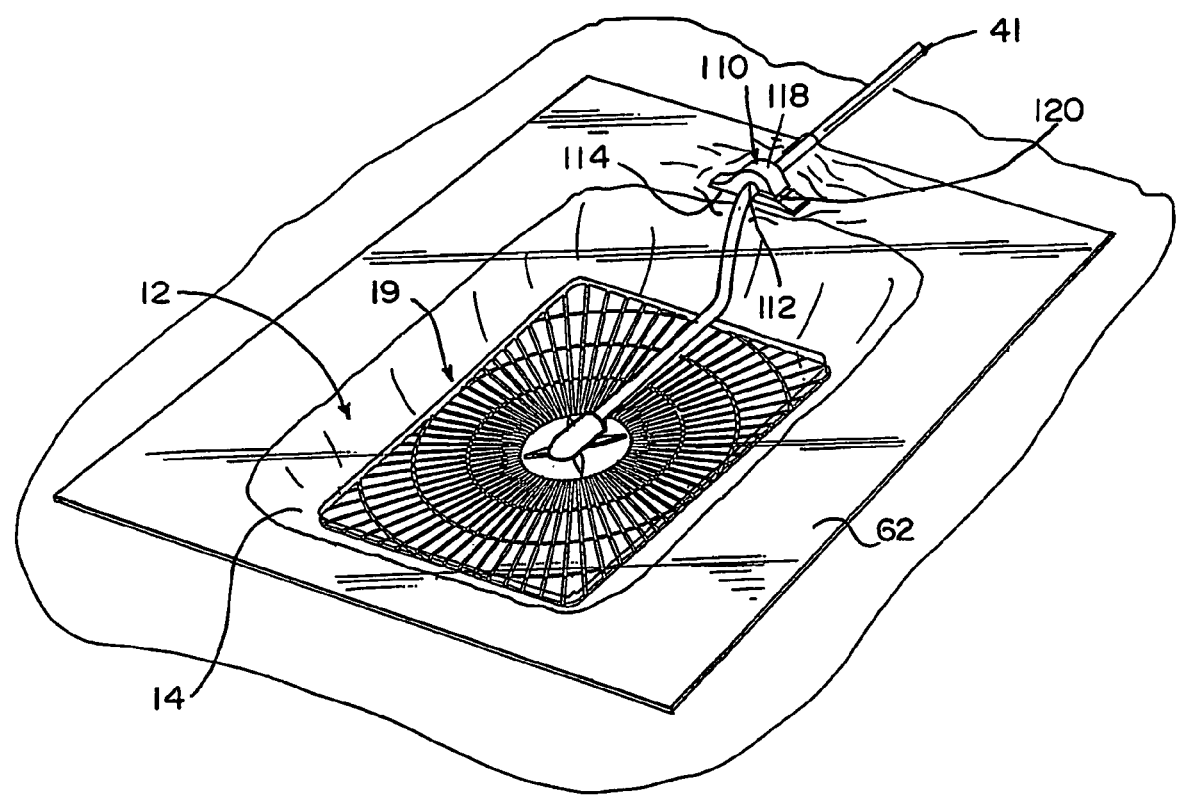
FIG. 12 is a perspective view of the bandage within the wound bed of a patient and showing the tube guide of FIGS. 10 and 11 coupled to the patient's healthy skin adjacent the wound and receiving the tube therethrough.

A tube guide 110, shown in FIGS. 10-12, is also provided in illustrated kit 10. Tube guide 110 has an aperture 112 for receiving a portion of vacuum/irrigation tube 41. As mentioned above, tube 41 is in communication with port 52 of member 19 and with the vacuum and/or irrigation source 16, 18. Tube guide 110 aides in effectively sealing the film 22 around tube 41 and to the patient's healthy skin 62 around wound 12 to create a sealed environment beneath film 22 and above wound surface 14. Without the use of tube guide 110, film 22 is pinched around the tube 41 by the caregiver to seal the film 22 against the patient's healthy skin 62 surrounding wound 12. Tube guide 110 acts to prevent air leaks into the vacuum space created below film 22.

Guide 110 is manufactured from a low durometer or soft polymer such as PVC, for example. In one embodiment, guide 110 has a width 111 of approximately 1 inch (2.54 cm), a height 113 of approximately ⅜ inch (9.525 mm), and a depth 115 of approximately ⅜ inch (9.525 mm). As shown in FIGS. 10 and 11, aperture 112 of guide 110 has a diameter of ¼ inch (6.35 mm) and is therefore designed to accommodate a vacuum/irrigation tube having a ¼ inch (6.35 mm) outer diameter. It is within the scope of this disclosure, however, to include a guide 110 having any suitable width, height, and depth and including an aperture having any suitable diameter for receiving vacuum/irrigation tubes of various sizes.

Guide 110 includes a flat bottom surface 114 having a pre-applied adhesive 116, as shown in FIG. 13. As shown in FIG. 14, bottom surface 114 is adhered to the healthy skin 62 adjacent wound 12. Guide 110 further includes a curved top surface 118. The bell-shaped contour of top surface 118 allows the sealing film 22 to drape over tube guide 110 and tube 41, rather than be pinched underneath tube 41. Therefore, guide 110 allows a more effective seal to be created around tube 41. The bell-shaped contour of top surface 118 includes a convex upper region 117 that blends smoothly into curved lower regions 119 which terminate at thin end edges 121 adjacent the patient's skin 62.

Guide 110 has a slit or opening 120 between a first surface 122 and a second surface 124 of guide 110. Opening 120 is in communication with aperture 112. As shown in FIGS. 12 and 13, surfaces 122 and 124 are parallel with respect to each other and are inclined with respect to the bottom surface 114. Opening 120 provides access to aperture 112. Tube 41 is placed within aperture 112 by separating surfaces 122, 124 away from each other and sliding tube 41 through the enlarged opening 120 to be received within aperture 112. A diameter of aperture 112 is approximately the same as an outer diameter of tube 41 to create a generally air tight seal between tube guide 110 and tube 41 to prevent outside air from the atmosphere around bandage 11 from entering the space above the wound 12 and possibly contaminating the wound surface 14. Opening 120 causes guide 110 to be flexible such that surfaces 122, 124 are movable relative to the bottom portion 114 and are urged to abut each other when sealing film 22 is placed over guide 110.

Sealing film 22 is placed over the wound 12 and seals against the curved top surface 118 of guide 110 rather than sealing directly against tube 41. As stated above, the contour of top surface 118 allows film 22 to drape over guide 110 to seal to top surface 118 of guide 110. Opening 120 is therefore sealed by film 22. It is also within the scope of this disclosure to extrude a vacuum/irrigation tube having the profile of the guide 110, thus eliminating the need for guide 110.

The components of kit 10 may be used in the following order. For example, the gloves 26 and other infection control garments may be used first. Next, the scissors 24 may be used to remove an old dressing, for example. A caregiver may next use a wound cleanser included in kit 10 to clean wound 12 and one of the cotton-tipped applicators 30 to measure the depth of the wound 12. Wound measurement device 32 may be used next, for example, to trace and record the perimeter of wound 12. Gauze 20 may next be used by the caregiver to clean the wound surface 14 or absorb fluid collected at the wound surface 14, for example. Skin protectant 34 may then be used to protect the patient's healthy skin 62 surrounding the wound 12. Next, the caregiver may place the member 19 on top of the wound surface 14 and finally cover the member 19 and the wound 12 with sealing film 22. The tape and patch sheet 94 may be used to repair any leaks which develop in the sealing film 22.

It is within the scope of this disclosure to package all components of kit 10 in sterile conditions so that each component of kit 10 is sterile and ready for use. It is further within the scope of this disclosure to package all components of kit 10 in such a manner that they are generally presented to the caregiver in the sequence that they are required during the dressing change of the wound 12, as described above. The packaging material of the kit 10 may be a thermo-formed, plastic tray with a clear polyurethane lid, for example. The tray may be formed to include individually shaped cavities to form pouches for each component.

Kit 10 may also include one or more vents, venting lines, valves, stopcocks, and multi-lumen tubes or tube sets. Vents or venting lines may be provided to circulate air through bandage 11, for example. Valves or stopcocks may be provided to direct flow between vacuum source 16 and bandage 11 and between irrigation source 18 and bandage 11, such as switch valve 55 diagrammatically illustrated in FIG. 1. Multi-lumen tubes may connect member 19, or another such wound dressing member, with vents and/or stopcocks. Multi-lumen tubes may provide multiple passageways for air, vacuum suction, and or irrigation fluids, for example. Such vents, stopcocks and multi-lumen tubes are disclosed in PCT International Publication No. WO 03/057070; which was filed concurrently herewith; which is titled VENTED VACUUM BANDAGE AND METHOD which is hereby incorporated by reference herein.

Kit 10 may also include wound inserts or wound packing for use with tunneled and/or undermined wounds, for example. Such inserts are provided to generally fill the open space created by various wound tunnels and/or undermined portions of wounds. Illustrative wound inserts are disclosed in PCT International Publication No. WO 2004/01820; which was filed concurrently herewith; which is title WOUND PACKING FOR PREVENTING WOUND CLOSURE which is hereby incorporated by reference herein.

Kit 10 may also include collars to provide external catheter access (for tube 41, for example) to vacuum bandage 11, and bandage packing to be placed between member 19 and sealing film 22. Illustrative collars and bandage packing can be found in PCT International Publication No. WO 03/073970; which was filed concurrently herewith; which is titled EXTERNAL CATHETER ACCESS TO VACUUM BANDAGE which is hereby incorporated by reference herein; and in PCT International Publication NO. WO 03/057071; which was filed concurrently herewith; which is titled VACUUM BANDAGE PACKING which is hereby incorporated by reference herein.

Although this invention has been described in detail with reference to certain embodiments, variations and modifications exist within the scope and spirit of the invention as described and defined in the following claims.

The invention claimed is:

1. A wound vacuum therapy dressing kit for use with a wound drainage system having a vacuum source, the kit comprising:
 a wound dressing member having a wound contacting surface configured to be in contact with and generally conform to a wound surface of a patient, the member being adapted to be coupled to the vacuum source for communicating suction from the vacuum source to the wound surface,
 a sealing film for placement over the member and configured to adhere to a patient's healthy skin surrounding the wound, and
 a wound measurement device comprising a perforated transparent film without adhesive including a first portion and a second portion removably coupled to the first portion and configured to be pulled from the first portion, the film configured to be folded such that (i) substantially all of a first surface of the first portion contacts a first surface of the second portion and (ii) the second surface of the second portion is configured for placement adjacent the wound surface, a second surface of the first portion including an exposed drawing surface and a grid that overlies the second portion when the first portion is folded relative to the second portion.

2. The kit of claim 1, further including a tube guide configured to be coupled to the healthy skin adjacent the wound and having an aperture configured to receive a portion of a vacuum tube of the wound vacuum drainage system that extends between the member and the vacuum source.

3. The kit of claim 2, wherein the tube guide includes a curved upper surface and the sealing film is configured to drape over and seal to the curved upper surface.

4. The kit of claim 3, wherein the tube guide includes a generally flat bottom surface and an adhesive layer coupled to the bottom surface.

5. The kit of claim 2, wherein the tube guide further includes a first end and a second end spaced apart from the first end to define an opening in communication with the aperture and configured to pass the vacuum tube therethrough for placement of the vacuum tube within the aperture.

6. The kit of claim 1, further including a patch sheet having a first adhesive layer and a second layer removably coupled to the first layer.

7. The kit of claim 6, wherein the first layer of the patch sheet includes patches and strips configured to be removed from the second layer of the patch sheet and placed over unwanted leaks in the film for use with the sealing film to seal about the member and create a vacuum space above the wound.

8. The kit of claim 7, wherein each of the patches has a diameter of ½ inch (12.7 mm), ¾ inch (19.05 mm), or 1 inch (2.54 cm).

9. The kit of claim 7, wherein each of the strips is 6 inches (15.24 cm) in length and has a width of ½ inch (12.7 mm), ¾ inch (19.05 mm), or 1 inch (2.54 cm).

10. The kit of claim 1, wherein the sealing film includes multiple release liners removably coupled to an adhesive back polyurethane layer.

11. The kit of claim 1, wherein the second portion of the wound measurement device includes a ruler.

12. The kit of claim 11, wherein the first portion of the wound measurement device further includes an information recording area for recording a patient's data information.

13. A wound vacuum therapy dressing kit for use with a wound drainage system having a vacuum source, the kit comprising:
 a generally non-compressible wound dressing member having a wound contacting surface configured to be in contact with and generally conform to a wound surface of a wound,
 a sealing film for placement over the member and configured to adhere to a patient's healthy skin surrounding the wound,
 a patch sheet having a first adhesive layer and a second layer removably coupled to the first layer, the first layer having a patches and strips configured to be removed from the second layer and placed over unwanted leaks in the film,
 infection control garments,
 applicators configured to measure a depth of the wound, and scissors configured to trim the member to fit the wound, wherein the kit further comprises a wound measurement device comprising a transparent film including a first portion and a second portion removably coupled to the first portion, the film configured to be folded such that (i) substantially all of a first surface of the first portion contacts a first surface of the second portion and (ii) the second surface of the second portion is configured for placement adjacent the wound surface, a second surface of the first portion including an exposed drawing surface and a grid that overlies the second portion when the first portion is folded relative to the second portion, and wherein the film is perforated.

14. A wound vacuum therapy dressing kit for use with a wound drainage system having a vacuum source, the kit comprising:

a wound dressing member having a wound contacting surface configured to be in contact with and generally conform to a wound surface of a patient, the member being adapted to be coupled to the vacuum source for communicating suction from the vacuum source to the wound surface, and a wound measurement device comprising a transparent film including a first portion and a second portion removably coupled to the first portion, the film configured to be folded such that (i) substantially all of a first surface of the first portion contacts a first surface of the second portion and (ii) the second surface of the second portion is configured for placement adjacent the wound surface, a second surface of the first portion including an exposed drawing surface and a grid that overlies the second portion when the first portion is folded relative to the second portion, wherein the film is perforated and wherein the film is configured to allow the second portion to be pulled from the first portion.

15. A wound vacuum therapy dressing kit for use with a wound drainage system having a vacuum source, the kit comprising:

a wound dressing member having a wound contacting surface configured to be in contact with and generally conform to a wound surface of a patient, the member being adapted to be coupled to the vacuum source for communicating suction from the vacuum source to the wound surface, and a wound measurement device comprising a transparent film including a first portion and a second portion removably coupled to the first portion, the film configured to be folded such that (i) substantially all of a first surface of the first portion contacts a first surface of the second portion and (ii) the second surface of the second portion is configured for placement adjacent the wound surface, a second surface of the first portion including an exposed drawing surface and a grid that overlies the second portion when the first portion is folded relative to the second portion, wherein the second portion of the wound measurement device includes a ruler.

16. The kit of claim 14, wherein the kit further comprises a tube guide configured to be coupled to healthy skin adjacent the wound and having an aperture configured to receive a portion of a vacuum tube of the wound drainage system that extends between the member and the vacuum source.

17. The kit of claim 16, wherein the tube guide includes a generally flat bottom surface and an adhesive layer coupled to the bottom surface.

18. The kit of claim 16, wherein the tube guide includes a generally convex top surface.

19. The kit of claim 14, wherein the member comprises a generally non-porous and generally non-compressible material.

20. The kit of claim 19, wherein the member is made of a medical grade silicone.

21. The kit of claim 19, wherein the wound contacting surface of the member includes holes in communication with the wound surface and the member further includes a port and a passageway between the port and each hole.

22. The kit of claim 13, wherein the second portion of the wound measurement device includes a ruler.

* * * * *